United States Patent [19]

Boyd et al.

[11] Patent Number: 5,674,691
[45] Date of Patent: Oct. 7, 1997

[54] METHOD OF SCREENING FOR LIGANDS TO A RECEPTOR-TYPE TYROSINE KINASE

[75] Inventors: Andrew W. Boyd, Ascot Vale; Richard John Simpson, Richmond; Ian Wicks, Kew; Larry David Ward, Balaclava; David Wilkinson, West Brunswick, all of Australia

[73] Assignee: Amrad Corporation Limited, Australia

[21] Appl. No.: 167,919

[22] PCT Filed: Jun. 19, 1992

[86] PCT No.: PCT/AU92/00294

§ 371 Date: Apr. 18, 1994

§ 102(e) Date: Apr. 18, 1994

[87] PCT Pub. No.: WO93/00425

PCT Pub. Date: Jan. 7, 1993

[30] Foreign Application Priority Data

Jun. 21, 1991 [AU] Australia .................... PK6841/91
Dec. 12, 1991 [AU] Australia .................... PK9992/91

[51] Int. Cl.$^6$ .................................. G01N 33/53
[52] U.S. Cl. .................. 435/7.2; 435/7.6; 435/7.91
[58] Field of Search ............... 435/7.2, 7.6, 7.91; 530/413

[56] References Cited

U.S. PATENT DOCUMENTS

| | | | |
|---|---|---|---|
| 5,447,860 | 9/1995 | Ziegler | 435/194 |
| 5,457,048 | 10/1995 | Pasquale et al. | 435/194 |
| 5,512,457 | 4/1996 | Lyman et al. | 435/69.5 |

FOREIGN PATENT DOCUMENTS

US91/05288  2/1992  WIPO.

OTHER PUBLICATIONS

Lhotak et al, "Characterization of Elk . . ." *Mol. Cell, Biol.* 11:2496–2502 (May 1991).

Hirai et al, "A Novel Putative Tyrosine Kinase Receptor . . ." *Science* 238:1717–1720 (Dec. 1987).

Pasquale et al, "Identification of chicken embryo kinase 5 . . ." *Cell Reg.* 2:523–534 (Jul. 1991).

Lindberg et al, "cDNA Cloning and Characterization . . ." Mol. Cell. Biol. 10(12):6316–6324 (Dec. 1990).

Sajjadi et al "Identification of a New eph–Related . . ." *New Biologist* 3(8):769–778 (Aug. 1991).

Flanagan et al "The kit Ligand: A Cell Surface Molecule . . ." *Cell* 63 63:185–194 (Oct. 1990).

Reeck et al "'Homology' in Proteins and Nucleic Acids . . ." *Cell* 50:667 (Aug. 1987).

Cantley et al "Oncogenes and Signal Transduction" *Cell* 64:281–302 (Jan. 1991).

*Primary Examiner*—Stephen Walsh
*Assistant Examiner*—Daryl A. Basham
*Attorney, Agent, or Firm*—Scully, Scott, Murphy & Presser

[57] ABSTRACT

The present invention relates to a method of screening for ligands to a receptor-type tyrosine kinase. The receptor-type tyrosine, in its naturally occurring form, is characterized by being reactive to monoclonal antibody III.A4, having an apparent molecular weight of approximately 120–150 kD in its glycosylated form, and having the N-terminal amino acid sequence E L I P Q P.

6 Claims, 24 Drawing Sheets

CATGGATGGTAACTTCTCCAGCAATCAGAGAGGCGCTCCCCCTCACATCAGTGGCATGCTTCATGGA

1.
M D C
GATATGCTCCTCTCACTGCCCTCTGCACCAGCAAC ATGGATTGT                                                 108

10                  20
Q L S I L L L S C S V L D S F G E L I P
CAGCTCCTCATCCTCCTCTCTTGCAGTCTGTTCTCGACAGCTTCGGG GAACTGATTCCGC

Q P S N E V N L L D S K T I Q
AGCCTTCCAATGAAGTCAATCTACTGGATTCAAAAACAATTCAA                                                  216

40                  50                  60
G E L G W I S Y P S H G W E E I S G V D E
GGGGAGCTGGGCTGGATCTCTTATCCATCACATGGGGTGGGAAGAGATCAGTGGTGTGGATGAAC

70
H Y T P I R T Y Q V C N V M D
ATTACACACCCATCAGGACTTACCAGGTGTGCAATGTCATGGAC                                                   324

80                      90
H S Q N N W L R T N W V P R N S A Q K I Y
CACAGTCAAAACAATTGGCTGAGAACAAACTGGGTCCCCAGGAACTCAGCTCAGAAGATTTATG

FIG 1a

```
                100                    110
V  E  L  K  F  T  L  R  D  C  N  S  I  P  L
TGGAGCTCAAGTTCACTCTACGAGACTGCAATAGCATTCCATTG 120                           130
V  L  G  T  C  K  E  T  F  N  L  Y  Y  M  E  S  D  D  D  H  G
GTTTTAGGAACTTGCAAGGAGACATTCAACCTGTACTACATGGAGTCTGATGATGATCATGGGG        540

140
V  K  F  R  E  H  Q  F  T  K  I  D  T  I  A
TGAAATTCGAGAGCATCAGTTTACAAAGATTGACACCATTGCA 150                              160
A  D  E  S  F  T  Q  M  D  L  G  D  R  I  L  K  L  N  T  E  I
GCTGATGAAAGTTTCACTCAAATGGATCTTGGGGACCGTATTCTGAAGCTCAACACTGAGATTA       648

170                              180
R  E  V  G  P  V  N  K  K  G  F  Y  L  A  F
GAGAAGTAGGTCCCTGTCAACAAGAAGGGATTTTATTTGGCATTT 190                                 200
Q  D  V  G  A  C  V  A  L  V  S  V  R  V  Y  F  K  K  C  P  F
CAAGATGTTGGTGCTTGTGTTGCCTTGGTGTCTGTGAGAGTATACTTCAAAAAGTGCCCATTTA       756

210
T  V  K  N  L  A  M  F  P  D  T  V  P  M  D
CAGTGAAGAATCTGGCTATGTTTCCAGACACGGTACCCATGGAC

FIG 1b
```

```
     220                                         230                        240
      S    Q   S   L   V   E   V   R   G   S    C   V   N   N   S   K   E   E   D   P   P
     TCCCAGTCCCCTGGTGGAGGTTAGAGGGTCTTGTGTCAACAATTCTAAGGAGGAAGATCCTCCAA               864

R   M   Y   C   S   T   E   G   E   W   L   V   P   I   G
     GGATGTACTGCAGTACAGAAGGCGAATGGCCTTGTACCCATTGGC 260                               270
      K   C   S   C   N   A   G   Y   E   E   R   G   F   M   C   Q   A   C   R   P   G
     AAGTGTTCCTGCAATGCTGGCTATGAAGAAAGAGGTTTTATGTGCCAAGCTTGTGACCAGGTT                  972

280                                   290
      F   Y   K   A   L   D   G   N   M   K   C   A   K   C   P
     TCTACAAGGCATTGGATGGTAATATGAAGTGTGCTAAGTGCCCG

P   H   S   S   T   Q   E   D   G   S   M   N   C   R   C   E   N   N   Y   F   R
     CCTCACAGTTCTACTCAGGAAGATGGTTCAATGAACTGCAGGTGTGAGAATAATTACTTCCGGG                 1080

A   D   K   D   P   P   S   M   A   C   T   R   P   P   S
     CAGACAAAGACCCCTCCATCCATGGCTTGTACCCGACCTCCATCT

330
      S   P   R   N   V   I   S   N   I   N   E   T   S   V   I   L   D   W   S   P
     TCACCAAGAAATGTTATCTCTAATATAAACGAGACCCTCAGTTATCCTGGACTGGAGTTGGCCCC
```

FIG 1c

```
      350
  L    D    T    G    G    R    K    D    V    T    E    F    N    I    I    C
  TGGACACAGGAGGCCGGAAAGATGTTACCTTCAACATCATATGT                              1188

K    K    C    G    W    N    I    K    Q    C    E    P    C    S    P    N    V    R    F    L    P
                       370                                 380
  AAAAAATGTGGGTGGAATATAAAACAGTGTGAGCCATGCAGCCCAAATGTCCGCTTCCTCCCTC           1296

R    Q    F    G    L    T    N    T    T    V    T    V    T    D    D    L
  GACAGTTTGGACTCACCAACACCACCGTGACAGTGACAGACCTT 400                              410                              420
  L    A    H    T    N    Y    T    F    E    I    D    A    V    N    G    V    S    E    L    S    S
  CTGGCACATACTAACTACACCTTTGAGATTGATGCCGTTAATGGGGTGTCAGAGCTGAGCTCCC           1404

430
  P    P    R    Q    F    A    A    V    S    I    T    T    N    Q    A
  CACCAAGACAGTTTGCTGCGGTCAGCATCACCACTAATCAGGCT 440                              450
  A    P    S    P    V    L    T    I    K    K    D    R    T    S    R    N    S    I    S    L    S
  GCTCCATCACCTGTCCTGACGATTAAGAAAGATCGGACCTCCAGAAATAGCATCTCTTTGTCCT           1512

460                              470
  W    Q    E    P    E    H    P    N    G    I    I    L    D    Y    E
  GGCAAGAACCTGAACATCCTAATGGGATCATATTGGACTACGAG

FIG 1d
```

```
    V K Y Y Y E K Q E Q E T S Y T I L R A R G T
    GTCAAATACTATGAAAAGCAGGAACAAGAAACAAGTTATACCATTCTGAGGGCAAGAGGCACAA    1620
  ▶ N V T I S S L K P D T I Y V F
    ATGTTACCATCAGTAGCCTCAAGCCTGACACTATATACGTATTA
    Q I R A R T A A G Y G T N S R K F E E T
    CAAATCCGAGCCCGAACAGCCGCTGGATATGGGACGAACAGCCGCAAGTTTGAGTTTGAAACTA
    S P D S F S I S G E S S Q V V GTGGTC
    GTCCAGACTCTTTCTCCATCTCTGGTGAAAGTAGCCAA GTGGTC                       1728
    M I A I S A V A I L L T V V I Y V L I
    ATGATCGCCATTTCAGCGGCAGTAGCCATTATTCTCCTCACTGTTGTCATCTATGTTTTGATTG
    G R F C G Y K S K H G A D E K
    GGAGGTTCTGTGGCTATAAGTCAAAACATGGGGCAGATGAAAAA
    R L H F G N G H L K L P G L R T Y V D P H
    AGACTTCATTTGGCAATGGGCATTTAAAACTTCCAGGTCTCAGGACTTATGTTGACCCACATA    1836
```

FIG 1e

```
              610
T  Y  E  D  D  P  T  Q  A  V  H  E  F  F  A  K  E
CATATGAAGACCCTACCCAAGCTGTTCATGAGTTTGCCAAGGAA                                   1944

620                                 •  •
L  D  A  T  N  I  S  I  D  K  V  V  G  A  G  E  F  G  E  V  C
TTGGATGCCACCAACATATCCATTGATAAAGTTGTTGGAGCAGGTGAATTTGGAGAGGTGTGCA

650
S  G  R  L  K  L  P  S  K  K  E  I  S  V  A
GTGGTCGCTTAAAACTTCCTCAAAAAAGAGATTTCAGTGGCC                                     2052

670
I  K  T  L  K  V  G  Y  T  E  K  Q  R  R  D  F  L  G  E  A  S
ATTAAAACCCTGAAAGTTGGCTACACAGAAAAGCAGAGAGACTTCCTGGGAAGCAAGCA

680
I  M  G  Q  F  D  H  P  N  I  I  R  L  E  G
TTATGGGACAGTTTGACCACCCCAATATCATTCGACTGGAAGGA                                   2160

700
V  V  T  K  S  K  P  V  M  I  V  T  E  Y  M  E  N  G  S  L  D
GTTGTTACCAAAAGTAAGCCAGTTATGATTGTCACAGAATACATGGAGAATGGTTCCTTGGATA 710                720
S  F  L  R  K  H  D  A  Q  F  T  V  I  Q  L
GTTTCCTACGTAAACACGATGCCCAGTTTACTGTCATTCAGCTA                                   2268
```

FIG 1f

```
                                    730                      740
     V  G  M  L  R  G  I  A  S  G  M  K  Y  L  S  D  M  G  Y  V  H
     CTGGGGATGCTTCGAGGGATAGCATCTGGCATGAAGTACCTGTCAGACATGGGCTATGTTCACC    2376

750
     R  D  L  A  A  R  N  I  L  I  N  S  N  L  V
     GAGACCTCGCTGCTCGGAACATCTTGATCAACAGTAACTTGGTG 760                    770            ◆
     C  K  V  S  D  E  G  L  S  R  V  L  E  D  D  P  E  A  A  Y  T
     TGTAAGGTTTCTGATTTCGGACTTTCGCGTGTCCTGGAGGATGACCCAGAAGCTGCTTATACAA    2484

T  R  G  G  K  I  P  I  R  W  T  S  P  E  A
     CAAGAGGAGGAAGATCCCAATCAGGTGGACATCACCAGAAGCT 800                              810
     I  A  Y  R  K  F  T  S  A  S  D  V  W  S  Y  G  I  V  L  W  E
     ATAGCCTACCGCAAGTTCACGTCAGCCAGTGATGTATGGAGTTATGGGATTGTTCTCTGGGAGG 820                                830
     V  W  S  Y  G  E  R  P  Y  W  E  M  S  N  Q
     TGATGTCTTATGGAGAGAGACCATACTGGGAGATGTCCAATCAG                        2592

D  V  I  K  A  V  D  E  G  Y  R  L  P  P  P  M  D  C  P  A  A
     GATGTAATTAAAGCTGTAGATGAGGGCTATCGACTGCCACCCCCATGGACTGCCCAGCTGCCT
```

FIG 1g

```
      861
L Y Q L M L D C W Q K D R N N
TGTATCAGCTGATGCTGGACTGCTGGCAGAAAGACAGGAACAAC                          2700
           880
R P K F E Q I V S I L D K L I R N P G S L
AGACCCAAGTTTGAGCAGATTGTTAGTATTCTGGACAAGCTTATCCGGAATCCCGGCAGCCTGA     2808
      890           900
K I I T S A A A R P S N L L L
AGATCATCACCAGTGCAGCCGCAAGGCCATCAAACCTTCTTCTG
                                     920
D Q S N V D I S T F R T T G D W L N G V R
GACCAAAGCAATGTGGATATCTCTACCTTCCGCACAACAGGTGACTGGCTTAATGGTGTCCGGA    2916
       930
T A H C K E I F T G V E Y S S
CAGCACACTGCAAGGAAATCTTCACGGGCGTGGAGTACAGTTCT
      940           950                960
C D T I A K I S T D D M K K V G V T V V G
TGTGACACAATAGCCAAGATTTCCACAGATGACATGAAAAAGGTTGGTGTGTCACCGTGGTTGGGC
           970
P Q K K I I S S I K A L E T Q
CACAGAAGAAGATCATCAGTAGCATTAAAGCTCTAGAAACGCAA                         3024
```

FIG 1h

```
       980                    P  P  V  *
S  K  N  G  P  V  P  V  *
TCAAAGAATGGGCCCAGTTCCCGTGTAAAGCACGACGGAAGTGCTTCTGGACGGAAGTGGTGGCT
GTGGAAGGCGTCAAGTCATCCTGCAGACAGACAATAATTCTGGA                    3132
```

FIG 1i

HEK ..MDCQLSILLLLSCSVLDSFGELIPQPSNEVNLLDSTKIQGELGWISYPSHGWEEISGVDE

ELK MAL--...L--F-LA-AVAAME-........T-M-TR-ATA----TAN-AS----V--Y--

HEK TFNLYYMESDDDHGVK....FREHQFTKIDTIAADESFTQMDLGDRILKLNTEIREVGPVNK

ELK -----Y-T-SVIAT-KSAFWS-APYL-V-------S-V-F-G-LM-V---V-SF--LTR

HEK SKEEDPP.RMYCSTEGEWLVPIGKCSCNAGYE.ERGFMCQACRPGFYKALDGNMKCAKCPPH

ELK AE-V-V-IKL--NGD----M----R-T-K----P-NSVA-K--PA-TF--SQEAEG-SH--SN

FIG 2a

```
HYTPIRTYQVCNVMDHSQNNWLRTNWVPRNSAQKIYVELKFTLRDCNSIPLVLGTCKE        118
NLNT------FEPN-----L-TFIN-RG-HR--T-MR--V---S-L-N-P-S---          108

KGFYLAFQDVGACVALVSVRVYFKKCPFTVKNLAMFPDTV.PMDSQSLVEVRGSCVNN       233
N------Y---MS-L----F-----SI-Q-F-V--E-MTGAE-T---IA--T-IP-         228

SSTQEDGSMNCRCENNYFRADKDPPSMACTRPPSSPRNVISNINETSVILDWSWPLDT       351
-RSPSEA-PI-T-RTG-Y---F---EV---SV--G-----IV----I--E-HP-RE-        348
```

FIG 2b

HEK  GGRKDVTFNIICKKCGWNIKQCEPCSPNVRFLPRQFGLTNTTVTVTDLLAHTNYTFEIDAVN
ELK  ---D----Y-------RADRRS-SR-DD--E-V----L----ECR-SISS-W----P----D-Q-I-

HEK  VKYYEKQEQETSYTILRARGTNVTISSLKPDTIYVFQIRARTAAGYGTNSRKFEFETSPDSFSI
ELK  IR----EHN-FNSSMA-SQTNTAR-DG-R-GMV--V-V----V----KF-G-MC-Q-LT-DDYK

HEK  LPGLRTYVDPHTYEDPTQAVHEFAKELDATNISIDKVVGAGEEGEVCSGRLKLPSKKEISVA
ELK  .--MKI-I--F-----NE--R------I-VSFVK-EE-I------YK-----G-R--Y---

FIG 2c

```
GVSELSSPPRQFAAVSITTNQAAPSPVLTIKKDRTSRNSISLSWQEPEHPNGIILDYE    471
---SK-PF-P-HVS-N-------T-PIMHQVSATMR--T---PQ--Q-------      468

SGESSQVVMIAISAAVAIILLT..VVIYVLIGRFCGYKSKHGADEKRLHFGNGHLK     589
-ELRE-LPL---G---AGVVFVVSL-A-SIVCS-KRA-SKEAVYSD-LQ-YST-RGS   588

IKTLKVGYTEKQRRDFLGEASIMGQFDHPNIIRLEGVVTKSKPVMIVTEYMENGSLDS  709
-----A--S---------------------------R----I--F----A---       707
```

FIG 2d

HEK  FLRKHDAQFTVIQLVGMLRGIASGMKYLSDMGYVHRDLAARNILINSNLVCKVSDFGLSRVLEDD.

ELK  ---QN-G---------------A---E-N----------V------------Y-Q--T

HEK  MSNQDVIKAVDEGYRLPPPMDCPAALYQLMLDCWQKDRNNRPKFEQIVSILDKLIRNPGS

ELK  ------N-IEQD---------H-----------S--R-AE--NT---M----A-

HEK  TDDMKKVGVTVVGPQKKIISSIKALETQSKNGPVPV*

ELK  SE-LLRI---LA-H----L----HSMRV-MNQS-SVMA*

FIG 2e

PEAAYTTR.GGKIPIRWTSPEAIAYRKFTSASDVWSYGIVLWEVMSYGERPYWE 827

SDPT---SSL-----V----A-------------------M-----F------D 827

LKIITSAAARPSNLLLDQSNVDISTFRTTGDWLNGVRTAHCKEIFTGVEYSSCDTIAKIS 947

--TVATIT-V--QP----R-IP-FTA-T-VD----SAIKMVQYRDS-LTAGFT-LQLVTQMT 947

FIG 2f 5,674,691

METHOD OF SCREENING FOR LIGANDS TO A RECEPTOR-TYPE TYROSINE KINASE

The present invention relates generally to a novel receptor-type tyrosine kinase and to genetic sequences encoding same.

Tyrosine kinases form an important class of molecules involved in the regulation of growth and differentiation (1). One mode of proof for this role came from the identification of receptors which bind known soluble growth factors. The receptors for epidermal growth factor (EGF) (2), platelet derived growth factor (PDGF) (3) and colony stimulating factor-1 (CSF-1)(4) were all shown to be transmembrane molecules with the cytoplasmic regions encoding a tyrosine kinase catalytic domain. The CSF-1 receptor is homologous to the PDGF receptor in both the catalytic and extracellular domains (1,5). The extra cellular domain of these proteins is distinguished from other tyrosine kinases by the presence of immunoglobulin-like repeats (1,6). Based on structural properties of the kinase domain, the c-kit protein was identified as another member of this family (7). The c-kit gene locus appears to underpin the defects in the congenitally anaemic W/W mouse (8–10). The ligand has now been identified (11–14) as shown to be encoded by the Sl locus. The locus is abnormal in the Steel mouse (15) which has identical defects to the W/W mouse but encodes a normal c-kit gene.

The other line of evidence for a critical role of tyrosine kinase proteins in growth control came from the study of vital oncogenes (16–17). These genes were shown to be directly involved in growth dysregulation by observations of a change in cell growth following introduction of DNA encoding these genes into fibroblasts. All oncogenes have been shown to have close cellular homologues (proto-oncogenes). One of the first identified oncogenes was v-src, the cellular homologue (c-src) is the prototypical representative of the family of cytoplasmic tyrosine kinases which, following myristylation, become associated with the inner leaf of the cell membrane (18). Within the haemopoietic system a number of lineage-restricted src-like kinases have been defined (19).

The T cell-associated src-like kinase, lck, has been shown to associate independently with both the CD4 and CD8 transmembrane glycoproteins to form a signalling complex (20,21). By contrast, v-erb-B and v-fms, like their cellular homologues the EGF receptor and CSF 1 receptor, respectively, are transmembrane molecules encoding the entire signal transduction machinery in a single polypeptide (1,17).

Detailed analysis of the amino acid sequences of these proteins has revealed conserved structural motifs within the catalytic domains (5). Both tyrosine and serine-threonine kinases have a consensus GXGXXG sequence (SEQ ID NO:12) which is found in many nucleotide binding proteins (5). Other conserved sequence motifs are shared by both types of kinase while others are specific for the tyrosine or the threonine-serine kinase subgroups (5). The tyrosine kinases, while having regions of sequence conservation specific to this family, can be further subdivided according to the structural features of the regions 5' to the catalytic domain (1,4–7). The novel tyrosine kinase of the present invention exhibits the same general characteristics as previously known tyrosine kinases.

In accordance with the present invention, a new receptor-type tyrosine kinase is provided and which is identified as a member of the eph/elk family of tyrosine kinases (22,23). The novel tyrosine kinase receptor is designated HEK ("human eph/elk-like kinase"). As the present inventors have identified expression of HEK in both pre-B and T cell lines, the receptor molecule of the present invention and/or its ligand is contemplated herein to have particular applicability for use as agents in the in vivo modulation of the production and/or function of pre-B, B and T cells.

Accordingly, one aspect of the present invention provides an isolated receptor-type tyrosine kinase, said tyrosine kinase characterised by, in its naturally occurring form, being reactive to the monoclonal antibody III.A4, having an apparent molecular weight of approximately 120–150 kD in the glycosylated form and having an N-terminal amino acid sequence SEQ ID No:1 comprising:

E L I P Q P.

Preferably, the tyrosine kinase has an N-terminal amino acid sequence SEQ ID NO:2 comprising:

E L I P Q P S N E V N L X D, wherein X is any amino acid and is preferably L.

More preferably, the tyrosine kinase has an N-terminal amino acid sequence comprising the amino acids:

E L I P Q P S N E V N L X D (S) K $X^1$ I Q, SEQ ID NO:3 wherein X and $X^1$ are any amino acid and preferably L and T, respectively.

Even more preferably, the tyrosine kinase comprises the amino acid sequence set forth in FIG. 1 or any parts or portions thereof, or having an amino acid sequence with at least 30% homology to the amino acid sequence set forth in FIG. 1 and having the identifying characteristics of HEK. More preferably, the degree of homology is at least 40%, still more preferably at least 55, even more preferably at least 70% and still even more preferably greater than 80%.

The hybridoma producing the monoclonal antibody III.A4 was deposited at Public Health Laboratory Service, European Collection of Animal Cell Cultures, Porton Down Salisbury, UK, on 20 Jun., 1991 under accession number 91061920.

The term "isolated" as used in relation to the tyrosine kinase of the present invention includes a biologically pure preparation comprising at least 20%, preferably at least 40%, more preferably at least 60% and even more preferably at least 80% of the protein relative to other molecules as determined by weight, activity or other convenient means. The term also encompasses any form of the protein not in the naturally occurring state such as, but not limited to, a preparation of membranes containing the protein, a preparation of the protein separate from the membrane or a supernatant fluid comprising said protein. The preparation may be glycosylated, partially unglycosylated or complete unglycosylated or may have a glycosylation pattern altered from what is naturally occurring.

The tyrosine kinase of the present invention is expressed on a number of tumours of human origin. In particular, data are presented herein showing HEK expression in human lymphoid tumour cell lines LK63, Lila-1, JM, MOLT4 and HSB-2 and the human epithelial tumour HeLa. One skilled in the art, however, will immediately recognise that similar or homologous kinases may exist on non-tumour cells or on non-human tumours and which have similar properties to the tyrosine kinase of the present invention. For example, the results contained herein show some expression of HEK in heart muscle. Accordingly, the present invention extends to a tyrosine kinase functionally and structurally similar in any or all respects to the tyrosine kinase herein described including a kinase of non-tumour origin.

The present invention extends to preparations comprising the naturally occurring form of the tyrosine kinase protein, including any naturally occurring derivative forms thereof, as well as to synthetic and recombinant forms of the protein including any single or multiple amino acid substitutions, deletions and/or insertions to the polypeptide portion of the kinase and to analogues and homologues thereof. Such amino acid alterations to the molecule are examples of recombinant or synthetic mutants and derivatives of the kinase.

Insertions include amino acid and/or carboxyl terminal fusions as well as intra-sequence insertions of single or multiple amino acids. Generally, insertions within the amino acid sequence will be smaller than amino or carboxyl terminal fusions, of the order of say 1 to 4 residues. Insertional amino acid sequence variants are those in which one or more amino acid residues are introduced into a predetermined site in the protein. Deletional variants are characterised by the removal of one or more amino acids from the sequence. Substitutional variants are those in which at least one residue in the sequence has been removed and a different residue inserted in its place. Such subsitutions generally are made in accordance with the following Table 1.

TABLE 1

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Generally amino acids are replaced by other amino acids having like properties, such as hydrophobicity, hydrophilicity, electronegativity, bulky side chains, etc.

Amino acid substitutions are typically of single residues; insertions usually will be on the order of about 1–10 amino acid residues; and deletions will range from about 1–20 residues. Deletions or insertions preferably are made in adjacent pairs, i.e.: a deletion of 2 residues or insertion of 2 residues.

The amino acid variants referred to above may readily be made using peptide synthetic techniques well known in the art, such as solid phase peptide synthesis (Merrifield; J. Am. Chem. Soc., 85: p2149, 1964) and the like, or by recombinant DNA manipulations. Techniques for making substitution mutations at predetermined sites in DNA having known sequence are well known, for example M13 mutagenesis. The manipulation of DNA sequences to produce variant proteins which manifest as substitutional, insertional or deletional variants are well known in the art and are described for example in Maniatis et al (Molecular Cloning: A Laboratory Manual; Cold Spring Harbor Laboratory, 1982).

Other examples of recombinant or synthetic mutants and derivatives of the tyrosine kinase protein of this invention include single or multiple substitutions, deletions and/or additions to any molecule associated with the kinase such as carbohydrates, lipids and/or proteins or polypeptides. Furthermore, it is possible that the tyrosine kinase protein of the present invention is a genetically altered version of a similar protein on normal cells. The present invention, therefore, extends to the tyrosine kinase protein from tumour or non-tumour origin and to all genetically altered forms thereof.

The terms "analogues" and "derivatives" extend to any functional chemical equivalent of the tyrosine kinase protein characterised by its increased stability and/or efficacy in vivo or in vitro. The terms "analogue" and "derivatives" also extend to any amino acid derivative of the tyrosine kinase protein as described above.

Analogues of HEK contemplated herein include, but are not limited to, modifications to side chains, incorporation of unnatural amino acids and/or derivatising the molecule and the use of crosslinkers and other methods which impose conformational constraints on the peptides or their analogues. Examples of side chain modifications contemplated by the present invention include modifications of amino groups such as by reductive alkylation by reaction with an aldehyde followed by reduction with NaBH4; amidination with methylacetimidate; acylation with acetic anhydride; carbamoylation of amino groups with cyanate; trinitrobenzylation of amino groups with 2, 4, 6 trinitrobenzene sulphonic acid (TNBS); acylation of amino groups with succinic anhydride and tetrahydrophthalic anhydride; and pyridoxylation of lysine with pyridoxal-5'-phosphate followed by reduction with NaBH$_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbomoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidaxole ring of a histidine residue may be accomplished by alkylation with iodoacetic acid derivatives or N-carbethoxylation with diethylpyrocarbonate.

Examples of incorporating unnatural amino acids and derivatives during protein synthesis include, but are not limited to, use of norleucine, 4-amino butyric acid, 4-amino- 3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bufinctional reagents which usually contain an amino-reactive moiety such as N-hydroxysuccinimide and another group specific-reactive moiety such as maleimido or dithio moiety (SH) or carbodiimide (COOH). In addition, peptides could be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention, therefore, extends to peptides or polypeptides and amino acid and/or chemical analogues thereof having the identifying characteristics of HEK as broadly described herein, and/or to regions thereof capable of, or responsible for, its action in transducing signals or in stimulating cellular responses such as growth and/or differentiation.

Accordingly, reference herein to the receptor-type tyrosine kinase of the present invention includes the naturally occurring molecule, recombinant, synthetic and analogue forms thereof and to any mutants, derivatives and human and non-human homologues thereof. All such kinases are encompassed by the term "HEK".

The present invention further extends to the ligand for the novel receptor-type tyrosine kinase described herein and to any agonists and antagonists (e.g. soluble form of the receptor) of the enzyme. Since the tyrosine kinase is an oncogenic protein, antagonists to the receptor are of particular relevance and fall within the scope of the present invention. Such antagonists include antibodies (monoclonal and polyclonal), the enzyme itself in soluble form or otherwise, specific peptides, polypeptides or proteins and carbohydrates, amongst others. These types of antagonists are useful in developing anti-tumour agents where the growth or maintenance of the tumour itself is supported by the tyrosine kinase of the present invention. Accordingly, the addition of an effective amount of an antagonist to the tumour-associated receptor-type tyrosine kinase will inhibit, reduce or otherwise interfere with the receptor activity of the protein and thus prevent, reduce and/or inhibit tumour growth. The present invention, therefore, extends to pharmaceutical compositions comprising one or more antagonists to the tyrosine kinase herein described and one or more pharmaceutically acceptable carriers and/or diluents.

Ligand(s) for HEK are capable of being screened for in a number of ways. In one protocol, an expression vector (e.g. AP-TAG-HEK) is selected which encodes the entire extracellular region of HEK fused to an appropriate reporter molecule like alkaline phosphatase. The fusion protein expressed in cells is recovered from cell supernatants and used to stain (using the reporter molecule) tissue sections using the methods as described by Flanagan and Leder (39), the disclosure of which is incorporated herein by reference. For example, the fusion protein is incubated with cells suspected of bearing the ligand under conditions whereby the fusion protein forms a complex with the cell-bound ligand. The cells are washed to remove unbound fusion protein, and then assayed for reporter activity. Once cellular sources of ligand are identified these cells are then used to construct an expression library. If the ligand is cell bound (eg membrane bound), the expression vector (eg AP-TAG-HEK) is used to stain pools to search for positive clones. If the HEK ligand is secreted, then another strategy will be required. In this case, supernatants of pools can be used to screen for induction of HEK phosphorylation in LK63 or HEK transfectants. Alternatively, supernatants from tissues producing HEK ligand can be used as a source in affinity purification on columns to which the product of, for example, pEE14-HEK is linked as a specific absorbent. The sequence of the purified ligand will be determined and this information used to clone the HEK ligand from cDNA libraries.

Another aspect of the present invention is directed to a nucleic acid isolate comprising a sequence of nucleotides encoding the novel receptor-type tyrosine kinase (including its recombinant, synthetic, mutant, derivative, analogue and homologue forms). The nucleic acid sequence may comprise deoxyribonucleotides or ribonucleotides and may exist in single or double stranded form, alone or in combination with a vector or expression vector molecule. The nucleic acid may be naturally occurring RNA or DNA or may be cDNA including complementary forms thereof. The nucleic acid molecule may also contain single or multiple nucleotide substitutions, deletions and/or additions relative to the nucleotide sequence encoding the naturally occurring or recombinant form of the protein. The vectors containing the nucleic acid sequences of the present invention may replicate in eukaryotes and/or prokaryotes and contain promoter sequences capable of expression in one or both of these types of cells. Suitable cells include mammalian, insect, yeast and/or bacterial cells. Particularly preferred cell types include CHO, baculovirus and E. coli cells. The preferred nucleotide sequence comprising HEK is set forth in FIG. 1. The general techniques of recombinant DNA technology, including isolation of recombinant proteins, are well known and are described for example in Maniatis et al (Supra).

This invention also provides a transgenic cell or cell culture carrying a nucleic acid isolate as described above.

In another aspect, this invention provides a pharmaceutical composition comprising a soluble form of the receptor-type tyrosine kinase as broadly described herein, said composition further comprising one or more pharmaceutically acceptable carriers and/or diluents.

This invention also extends to methods of use of the novel receptor-type tyrosine kinase of this invention and of antagonists to ligands binding to this tyrosine kinase.

In one aspect, this invention extends to a method of ameliorating the effects of interaction or binding between HEK and its ligand in a mammal comprising administering to said mammal an effective amount of the antagonist to a ligand binding to the tyrosine kinase of this invention.

The invention also extends to a method of phosphorylating a protein comprising contacting a preparation of said protein with an effective amount of the receptor-type tyrosine kinase of this invention for a time and under conditions sufficient to effect phosphorylation of the protein.

In yet another aspect, the invention provides a method of screening for a ligand bound to tissue or cells to the receptor-type tyrosine kinase of this invention comprising contacting the tyrosine kinase fused to a reporter molecule capable of producing a detectable signal to the tissue or cell sample to be tested for a time and under conditions sufficient for the fused tyrosine kinase to bind to a ligand on said tissue or cells and then detecting the reporter molecule.

The invention further provides a method of screening for a soluble ligand to the receptor-type tyrosine kinase of this invention comprising contacting a sample to be tested with a cell line capable of expressing the tyrosine kinase and screening for phosphorylation in said cell line.

One skilled in the art will, however, immediately recognise that a variety of mutations, derivatives or chemical alternations can be made to the sequence to encode, for example, the analogues and derivatives disclosed above. The present invention also extends to short nucleic acid molecules which can act as nucleic acid probes to screen for the presence of the HEK gene or mutations therein.

The present invention is further described with reference to the following non-limiting Figures and Examples.

EXAMPLE

1. Materials and Methods

Figure 1:
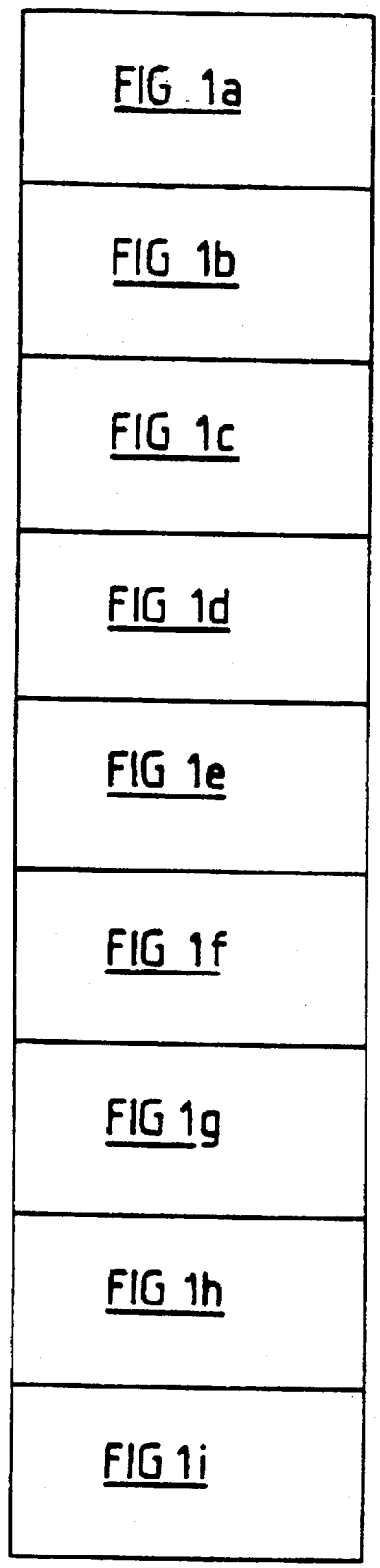
FIGS. 1a–1i represent the nucleotide sequence SEQ ID NO:9 and deduced amino acid sequence SEQ ID NO:10 of HEK coding sequence with partial 3' and 5' untranslated sequence. Numbers at right indicate positions of nucleotides and numbers above amino acids refer to amino acid sequence. A single underline indicates the presumed signal peptide. Double underline indicates the presumed transmembrane region. Dashed overline indicates identity between the predicted amino acid sequence and the sequence obtained from purified HEK protein. Triangles indicate potential sites for N-linked glycosylation within the extra-cellular domain. Dots indicate the putative ATP-binding site. The diamond indicates a putative autophosphorylation site. Asterisks indicate stop codons.

Cell lines, Mab III4 HEK protein structure and function

The LK63 and LK63/CD20+ cell lines were derived from a child with acute lymphoblastic leukaemia. LK63/CD20+ is a tetraploid variant of LK63, which arose spontaneously in vitro and has enhanced HEK expression. In contrast to the parental cell line, LK63/CD20+ expresses CD20. These lines have cytogenetic features of pre-B cell leukaemia and have not been transformed with Epstein-Barr virus (24). JM and HSB-2 are CD8+, human T cell leukaemic cell lines.

The IIIA4 Mab was generated against the LK63 cell line and recognised a 135 kD, cell surface molecule (HEK) with in vitro kinase activity expressed by LK63, LK63/CD20+ and JM (25).

The IIIA4 Mab was used to purify HEK antigen for amino acid sequencing (25). The amino acid sequences obtained were as follows, where doubtful residues are bracketed and unidentified residues are marked X: N terminus—SEQ ID NO:3 ELIPQPSNEVNLXD(S)KXIQ; internal— GYRLPPPMDCPAALYQLMLDC.

LK63 cDNA library construction and screening

A random primed cDNA library was constructed in λgt10 (Amersham) using 5 ug of poly A+ selected mRNA from LK63/CD20+ cells. A degenerate oligonucleotide was designed on the basis of the internal (3') HEK protein sequence. The neutral base inosine was included at positions of high codon degeneracy (26). The 51 mer: SEQ ID NO:5

```
TACCGICTICCICCICCIATGGACTGCCCIGCIGCICTITACCAA
  T             T T              T   G
          CTIATG
``` was end labelled using γ32P-deoxyadenosine triphosphate (ATP) and polynucleotide kinase, followed by separation on a G25 Sephadex column as previously described (27). Approximately 250,000 plaques were screened in 2×SSC (SSC=0.15M NaCl, 0.015M sodium citrate) hybridisation buffer at 37°, as previously described (27). Washes were performed in 2×SSC/0.1% w/v sodium dodecyl sulphate (SDS) at 42°–55°. The signal from one duplicating plaque persisted following 55° washes. The DNA from this plaque contained an insert of 2.5 kb (HEK 2.5). HEK 2.5 was labelled with $\alpha^{32}$P-ATP (Amersham random primer kit) for Northern blot analysis of LK63 cells. The polymerase chain reaction (PCR) was performed using HEK 2.5 and oligonucleotide primers based on conserved motifs within the catalytic domain of PTKs and the 3' amino acid HEK sequence, as previously described (28). HEK 2.5 was labelled with $\alpha^{32}$P-ATP (as above) and used to rescreen the random primed LK63 cDNA library in 2×SSC hybridisation buffer at 65°. Thirty two duplicating positives were isolated and screened by hybridisation with a degenerate oligonucleotide based on the N terminal HEK protein sequence. A 4.5 kb HEK clone (HEK 4.5) which hybridised with the N terminal oligonucleotide was chosen for complete characterisation.

DNA sequencing and analysis of HEK cDNA

HEK 4.5 was subcloned into pGEM7 which had been digested with EcoRI and treated with calf intestinal phosphatase. Double stranded DNA was purified on a caesium chloride gradient and used as the template in dideoxy chain termination sequence reactions (29). Sense and antisense oligonucleotide primers were used to complete sequencing with T7 DNA polymerase (Promega). Protein sequence alignment was performed using the GAP programme (University of Wisconsin, Genetics Computer Group).

Expression of HEK in COS cells

The HEK 4.5 EcoRI insert was blunt ended with Klenow DNA polymerase 1 and dATP plus dTTP, followed by ligation to BstXI adaptors. The adapted insert was ligated to BstXI digested CDM8 (30). Sense and antisense constructs were prepared and transfected into COS cells using DEAE-dextran/chloroquine with dimethyl sulphoxide (DMSO) (17). Two days post-transfection, COS cells were stained with IIIA4 followed by fluorescein isothiocyanate conjugated (FITC)-conjugated sheep anti-mouse immunoglobulin (Ig) (Silenus) and examined under a fluorescence microscope.

Northern and Southern blot analysis of cell lines

Poly A+ selected mRNA was isolated as previously described (31) and fractionated on a 1% formaldehyde agarose gel prior to transfer onto a HybondC extra membrane (Amersham). Filters were probed with HEK 4.5 and subsequently with a glyceraldehyde-3-phosphate dehydrogenase (GAPDH) insert as a control. DNA was prepared by lysis with guanidine hydrochloride (32), transferred to Zetaprobe membranes and hybridised under conditions suggested by the manufacturer (Bio-Rad). In order to minimise cross hybridisation with other tyrosine kinases in Southern analysis of genomic DNA, PCR was used to generate a 1.1 kb HEK probe which spans a less highly conserved region of the molecule (nucleotides 1,109 to 2,241, FIG. 1). The autoradiogram of the Southern blot was digitised using the MacScan programme on a Macintosh IIx computer.

Scatchard analysis of IIIA4 binding to cell lines

Binding of $^{125}$I labelled IIIA4 to cell lines was performed in competition with unlabelled IIIA4 as previously described (33).

Protein analysis

Figure 9:
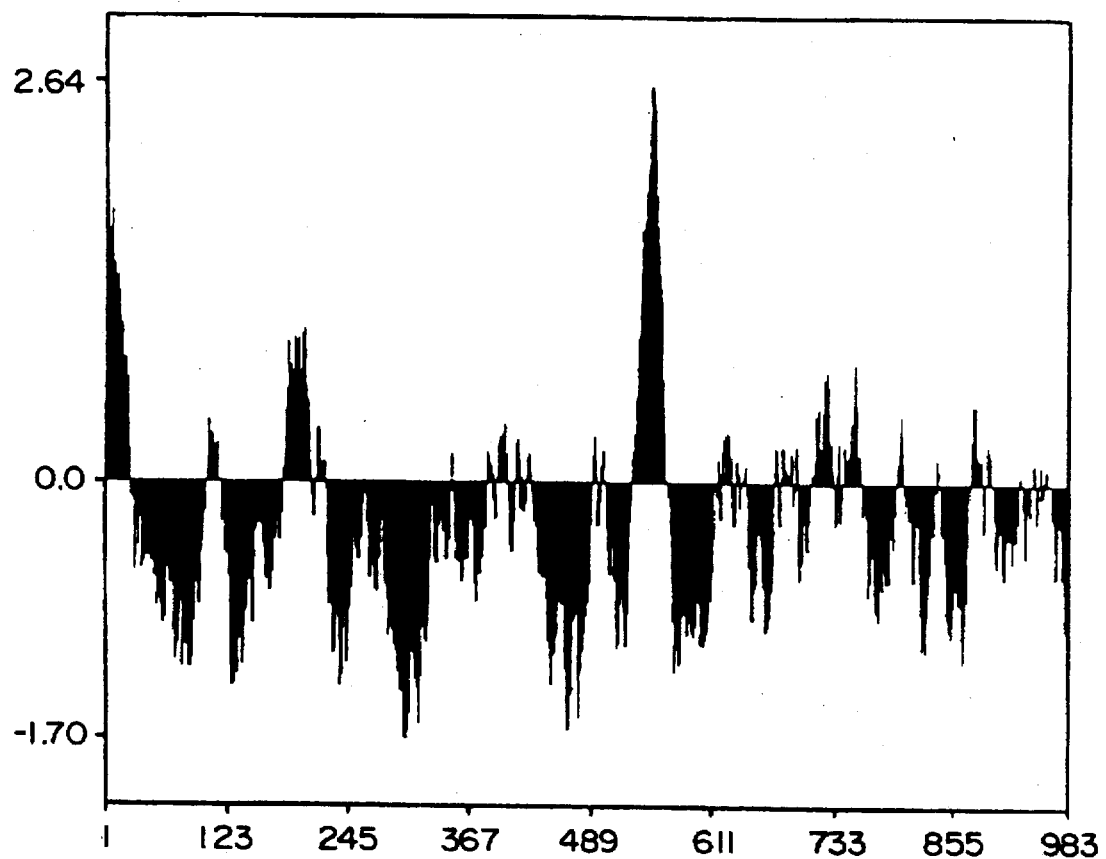
FIG. 9 is a graphical representation showing a hydropathy analysis (span length: 25) of the predicted translational product of the HEK 4.5 cDNA. The Y axis indicates a hydropathy index, with hydrophobic residues appearing above the origin and hydrophilic residues below. The AAs comprising the translated product of the HEK cDNA are numbered along the X axis from 1–983.

The HEK protein was subjected to hydrophobicity analysis as described by Kyte and Doolittle (40). The results are shown in FIG. 9.

Oligos to construct expression vectors encoding variants of the extracellular domain of HEK Primer HEK5'/92 has the following sequence: SEQ ID NO:6

```
       Bam H1  Eco R1
        ┌──┐  ┌────┐
     GTAGGGATCCGAATTCTGCACCAGCAACATG
              └────────────────────┘
```

The BamH1 and Eco R1 sites are indicated above the sequence and the underlined portion corresponds to positions 86 to 102 of the sequence set forth in FIG. 1.

Primer HEK/EE14/92 has the sequence: SEQ ID NO:7

```
       Bam H1
        ┌──┐
     GTAGGGATCCTACACTTGGCTACTTTCA
              └┘└─────────────────┘
              Stop  Codon
```

The underlined portion after the stop codon is the reversed and complemented sequence of nucleotide 1710–1725 of FIG. 1.

```
       Bam H1
        ┌──┐
     GCGGATCCTTGCCTACTTTCACCA   SEQ ID NO:8
              └────────────┘
```

The underlined sequence when reversed and complemented corresponds to 1708–1723 of the sequence in FIG. 1 and does not contain the stop codon permitting read through from the BamH1 site.

PCR Conditions

PCR was performed with Taq polymerase under standard conditions using CsCl purified pGEM7-HEK; which contains the full length HEK cDNA, as a template. Cycle times and temperatures:

60' at 97° C.
60' at 55° C.
90' at 73° C.

the reaction was carried out for ten cycles.

1. The 1.7 kb PCR product of the HEK5'/92 and HEK/EE14/92 was purified using Geneclean, digested with Eco R1 and BamH1 and cloned between the Eco R1 and Bcl I site of pEE14 (obtained from Celltech, Berkshire, UK).

Analysis showed the predicted 1.7 kb insert in the clones which were designated "pEE14-HEK".

2. The 1.7 kb PCR product of 5' HEK5'/92 and HEK/TAG/3' was digested with BamH1, cloned into BglII site of AP-Tag-1, Flanagan & Leder (39). Using SnaB1, the sense of the clones could be determined to fused clones with the correct orientation. The resulting clones were designated AP-TAG-HEK Expression pEE14-HEK was transfected into CHO cells and lines selected with methionine sulfoxime.

AP-TAG-HEK was transfected into 3T3 cells with pSV2 neo and clones selected with G418.

EXAMPLE

2. HEK

Isolation and characterisation of cDNA clones for HEK

One duplicating signal was obtained from screening approximately 250,000 plaques of an LK63-derived λgt10 cDNA library under relaxed conditions with a degenerate 51 mer oligonucleotide. This plaque contained a 2.5 kb insert (HEK2.5) which hybridised with a single 5.5–6.0 kb mRNA species in Northern blot analysis of cell lines expressing HEK i.e. LK63 and JM. PCR using HEK 2.5 and oligonucleotide primers based on conserved motifs within the catalytic domains of tyrosine kinases (28), gave DNA products of the appropriate size. These results indicated HEK 2.5 was truncated at the 5' end. HEK 2.5 was used to re-screen the library under more stringent conditions and a 4.5 kb HEK (HEK 4.5) clone isolated. This clone hybridised with a degenerate oligonucleotide based on the N terminal protein sequence and produced DNA bands of the predicted sizes in PCR reactions using the primers referred to above. These data indicated the 4.5 kb clone probably contained the complete HEK coding region.

The sequence of the coding region for HEK together with partial 3' and 5' untranslated sequence, is shown in FIG. 1. An open reading frame of 2,952 nucleotides extends from the initiation methionine at position 100 to the first termination codon at position 3051. Translation of the cDNA results in a predicted protein of 983 amino acids (AAs). There is identity between the AAs obtained by sequencing of purified HEK protein and the predicted AA product of the cDNA clone (see FIG. 1). The predicted molecular weight of the translated protein (minus the putative signal peptide) is 92.8 kD. This is in good agreement with previous results demonstrating a core protein of approximately 95 kD in both tunicamycin- and endoglycosidase-treated LK63 cells (25). The predicted protein product of the HEK cDNA clone has the features of a type 1a integral membrane protein (35). Two predominantly hydrophobic regions indiciate a putative signal peptide (AAs 1–20) and a transmembrane segment (AAs 542–565). The extracellular domain of 521 AAs contains five possible sites for N linked glycosylation. The N terminal region (AAs 21–376) of the extracellular domain is rich in cysteine residues. The C-terminal region (AAs 326–511) of the extracellular domain contains two repeats homologous to those found in fibronectin type III (36). The cytoplasmic domain (AAs 566–983) of HEK contains a typical ATP binding site (GXGXXG; SEQ ID NO:12) at AA positions 628–633 and a putative autophosphorylation site (E/DXXYXX; SEQ ID NOS:13,14) at position 779.

Figure 2:
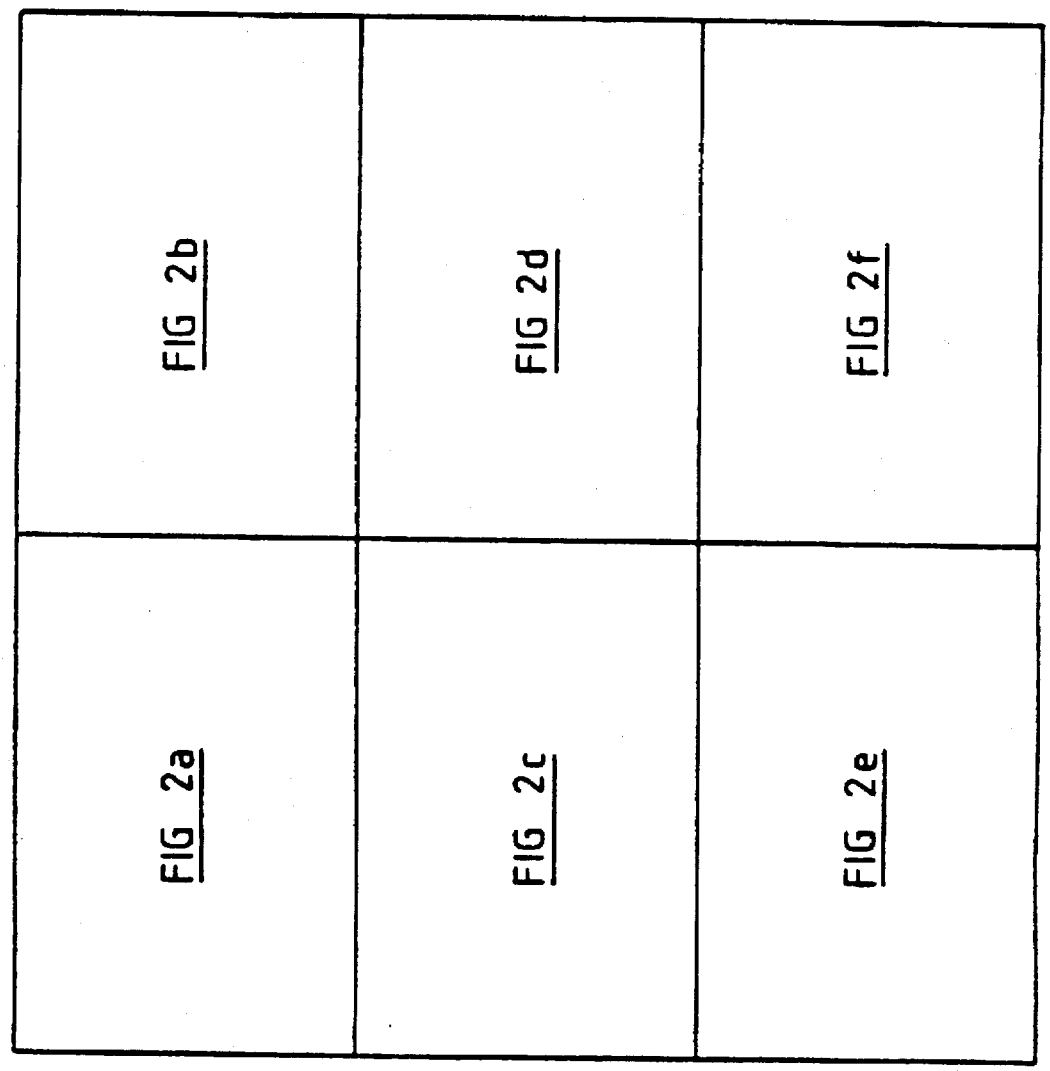
FIGS. 2a–2f represent the protein sequence alignment of HEK with elk SEQ ID NO:11, a related gene within the eph/elk family. Alignment was performed using the GAP programme. Amino acid positions are numbered on the right. Dots in the sequence indicate gaps introduced to optimise the alignment. Dashes indicate identity between amino acids. Asterisks indicate stop codons. Dots above the line of amino acids indicates residues contributing to the two repeats of homology with fibronectin type III, within the C-terminal regions of the extracellular domains. Triangles above the line of amino acids highlight conserved cyseine residues within the N-terminal region.

Protein sequence alignment shows a high degree of homology between HEK and eph, elk, eck, eek and erk in the catalytic domains. HEK has the following overall protein sequence homology with each of the three sequenced members of the eph RTK family: (chicken) CEK 56.4%, (rat) elk 56.1%; (rat) eck 50.6%; (human) eph 42.3%. Protein sequence alignment between HEK and a close relative ELK is shown in FIG. 2. The homology between these molecules is greatest within the catalytic domains. Outside the catalytic domains, numerous short motifs which may be of structural or functional significance, are conserved between HEK, eph, elk and eck, particularly towards the N terminus. There is strict conservation of the number and spatial arrangement of cysteine residues within the extracellular domains of HEK, eph, elk and eck (34). These cytokine residues cluster within the N terminal portion of the extracellular domains (36). The C terminal regions of the extracellular domains contain repeats which are homologous to those found in fibronectin type III (36). HEK has a cysteine in the C terminal tail (AA928), rather than the tyrosine which is conserved in this position between other members of the EPH/ELK family. This may be of significance in that phosphorylation of C terminal tyrosine residues can regulate tyrosine kinase activity (37). However HEK has a C terminal tyrosine at position 937, which also appears to be in a better context for autophosphorylation (38).

Transfection and expression of HEK in COS cells

Figures 3A, 3B:
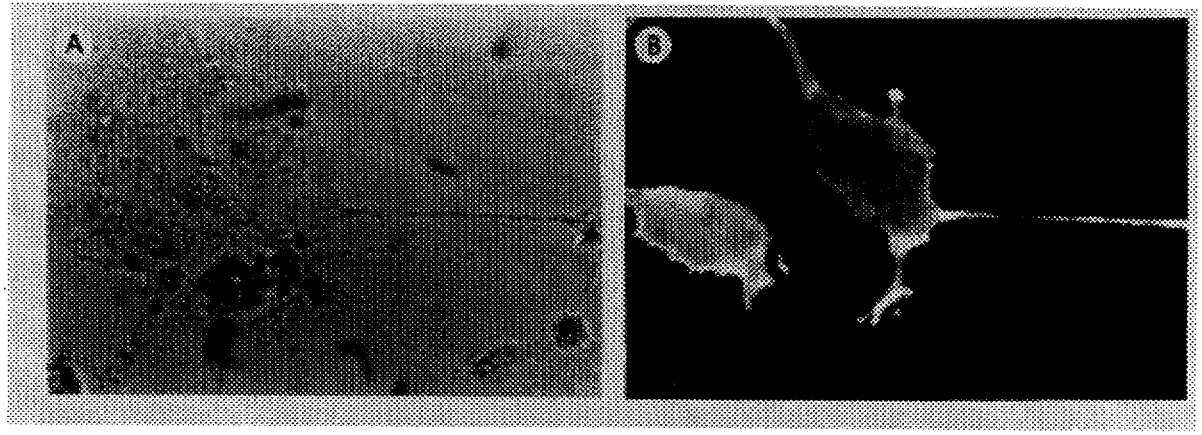
FIGS. 3a and 3b are photographic representations showing expression of HEK in COS cells. The HEK 4.5 kb cDNA clone was subcloned into the expression vector CDM8. COS cells were transfected with this construct using DEAE-dextran/chloroquine and DMSO. Two days after transfection cells were stained in situ with the IIIA4 MAb followed by FITC-conjugated sheep anti-mouse Ig and photographed under light microscopy (panel A), or fluorescence microscopy (panel B). Magnification ×400.

To demonstrate that the cDNA clone isolated did indeed encode the molecule recognised by the IIIA4 Mab, HEK 4.5 was subcloned into the expression vector CDM8 and transfected into COS cells in both sense and antisense orientations. As shown in FIG. 3, COS cells transfected with HEK in the sense orientation stained specifically with IIIA4, confirming that the cDNA clone contains the full coding sequence and is identical to the molecule recognised by IIIA4. COS cells transfected with HEK in the antisense orientation did not stain with IIIA4.

Expression of HEK in human lymphoid cell lines

Figure 4:
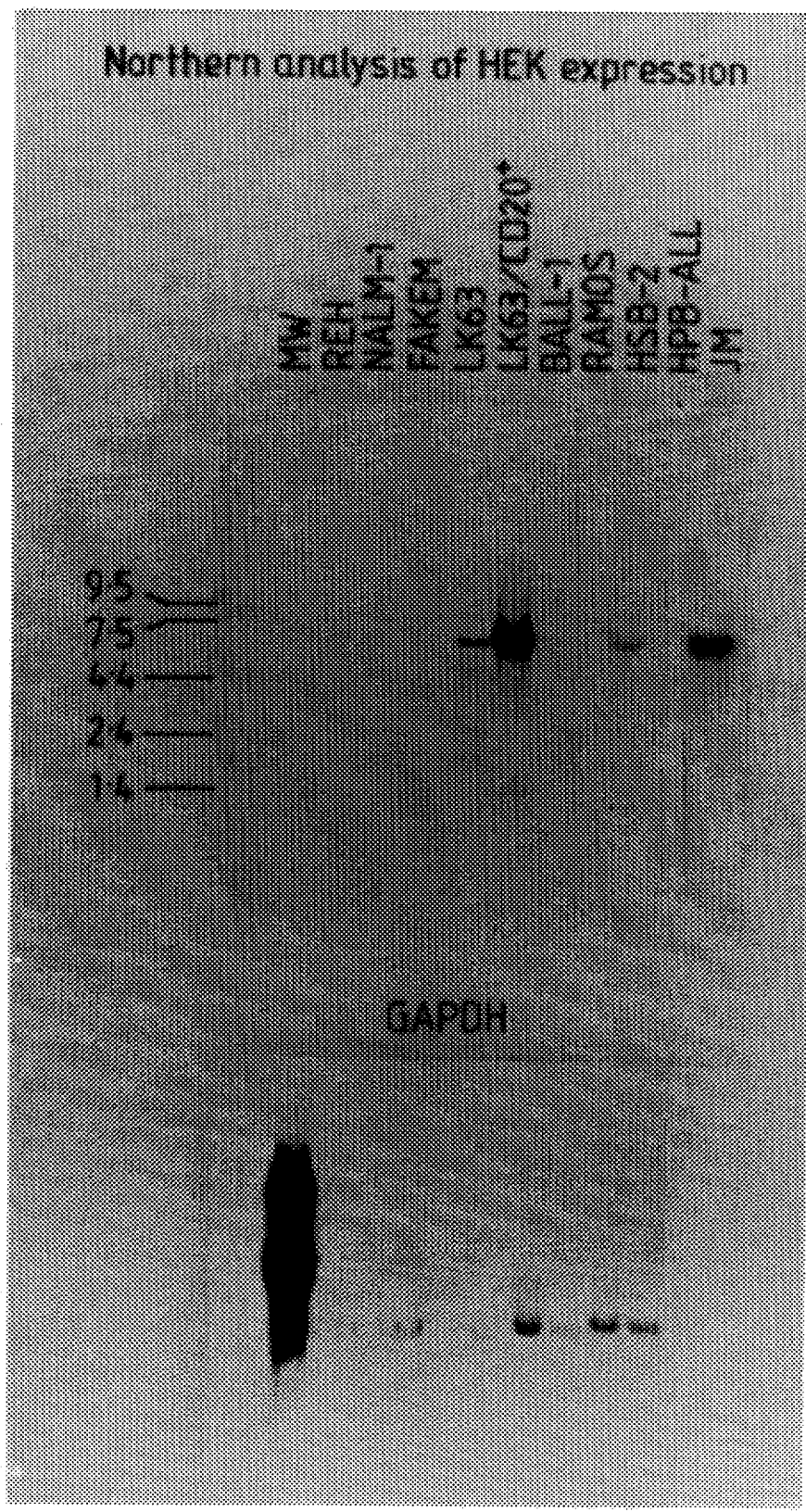
FIG. 4 is a photographic representation of Northern blot analysis of HEK expression in cell lines. Poly (A)+RNA from human cell lines was fractionated on an agarose/ formaldehyde gel and transferred onto Hybond-C extra membrane. The filter was hybridised with the HEK 4.5 kb cDNA (upper panel). The same filter was hybridised with GAPDH as a quantitative control (lower panel). REH, NALM-1 and FAKEM are pre-B leukaemic cell lines. BALL-1 is an early B leukaemic cell line. RAMOS is a mature B leukaemic cell line. HSB-2, HPB-ALL and JM are T leukaemic cell lines.
Figure 5:
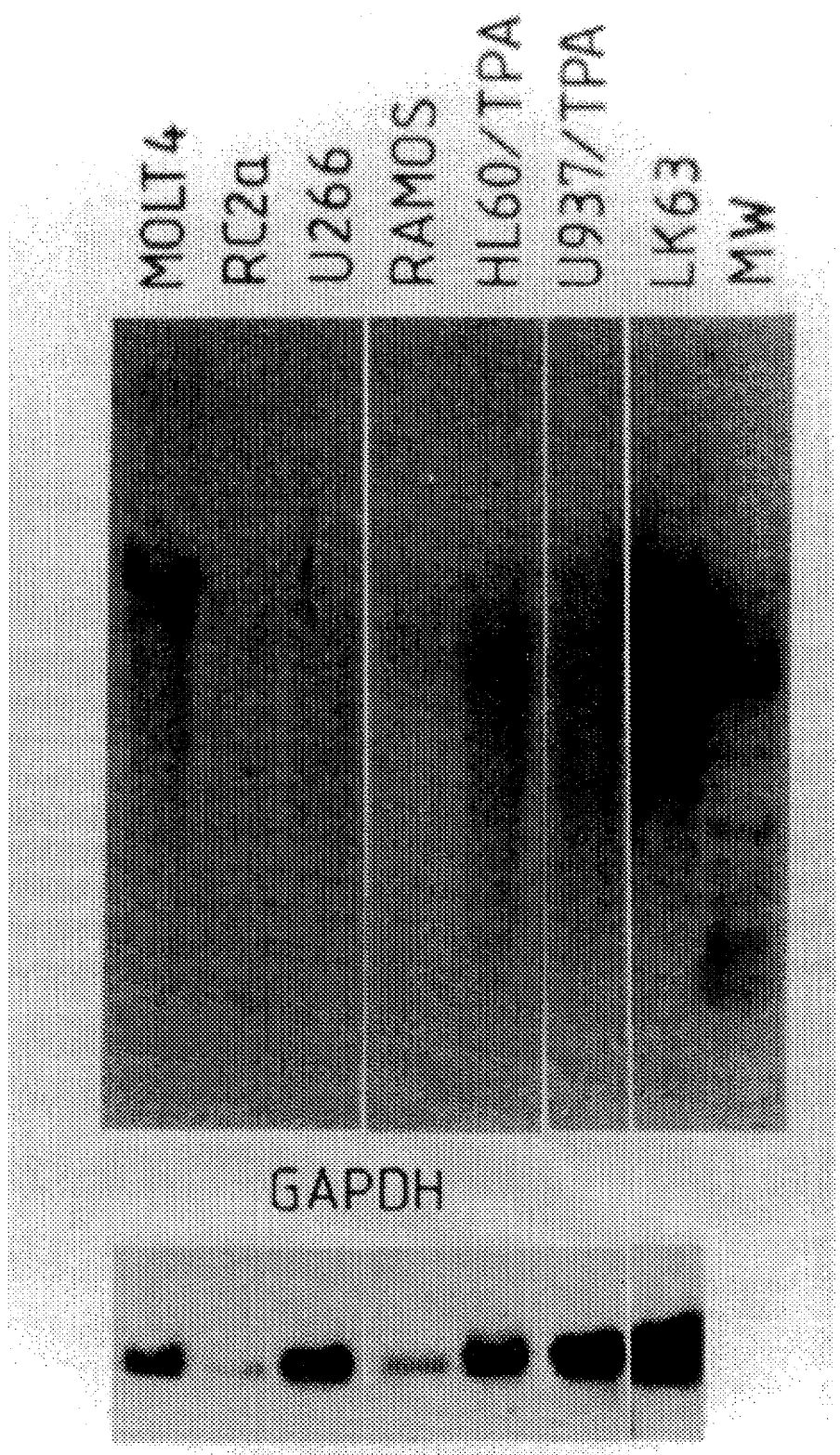
FIG. 5 is a photographic representation showing Northern blot analysis of HEK expression in cell lines. Poly A+ RNA from human cell lines was probed for HEK expression as above. Molt 4 is an immature T cell line. RC2a, HL60 and U937 are myelomonocytic cell lines. In this experiment, RNA was extracted from HL60 and U937 after treatment of cells with tetra decannoyl phorbol myristic acetate (TPA), an activator of protein kinase C. U266 is a mature B cell line.
Figure 6:
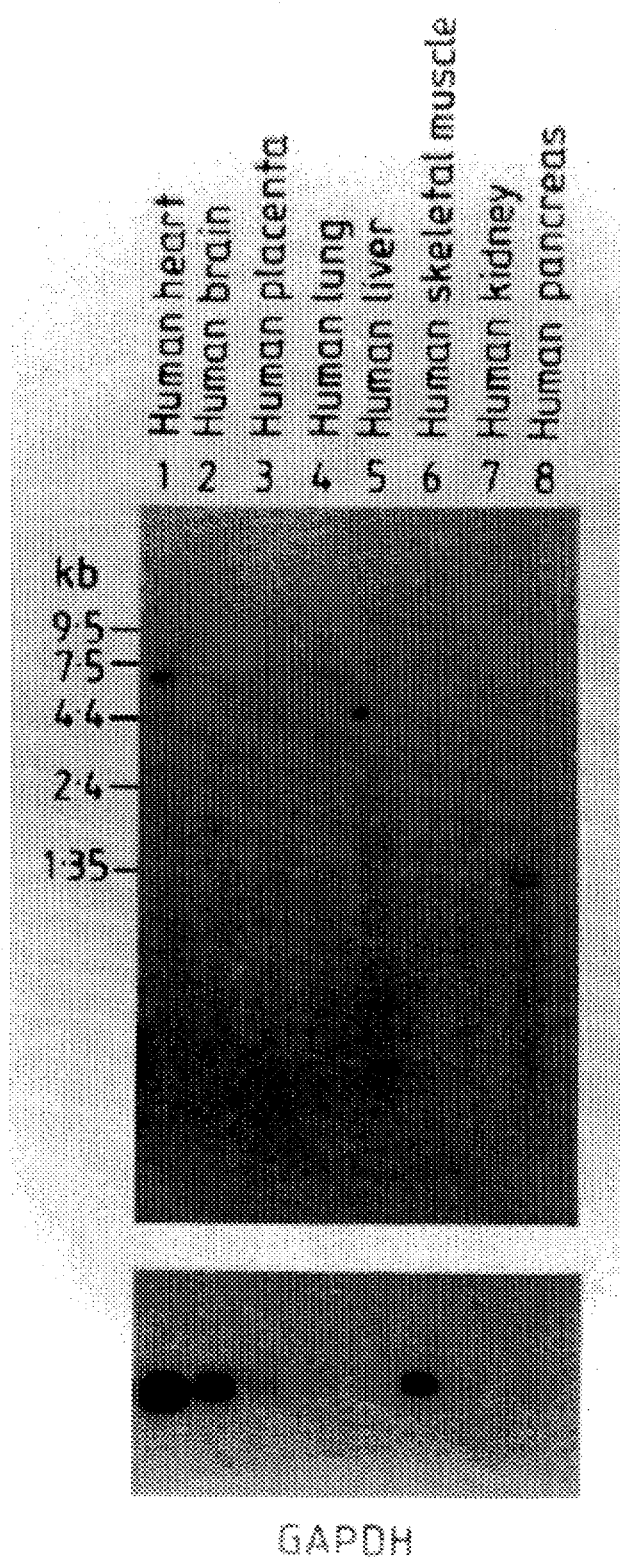
FIG. 6 is a photographic representation showing Northern analysis of HEK expression in adult post mortem tissues. A multiple tissue Northern blot was purchased commercially and probed for HEK expression under conditions suggested by the manufactuerer (Clontech). The 1.3 kb band in pancreas is too small to represent a transcript for a secreted form of HEK and is probably due to cross hybridisation.

Cell surface staining with IIIA4 revealed a highly restricted pattern of HEK expression on LK63—a pre B cell line, and JM—a T cell line. To further explore the expression of HEK, Northern blot analysis was performed with HEK 4.5 (FIGS. 4 to 6). A single 5.5–6.0 kb band was seen in both LK63 and JM cells. However there was a less intense band of the same size in another T cell line—HSB-2—which did not stain with IIIA4. Other cell lines in which HEK transcripts were detected include Lila-1, MOIT4 and HeLa. There were no HEK transcripts detected in a range of other cell lines although a weak band was seen in heart muscle (FIG. 6). The number of HEK molecules was determined on HSB-2, LK63/CD20+ and other cells using Scatchard analysis of IIIA4 MAb binding. The LK63/CD20+ cells had approximately 15,000 sites per cell and JM cells had 9,500 sites per cell. In contrast, HSB-2 had approximately 1,070 sites per cell, which is too low for detection by immunofluorescence against the autofluorescence background of this cell line. The affinity constants for antibody binding were in the range of $2.5-4.0 \times 10^9$. Raji and K562 cells showed no detectable antibody binding above background. Tables 1 and 2 summarise the phenotype of HEK expression cell lines.

Southern blot analysis

Figure 7:
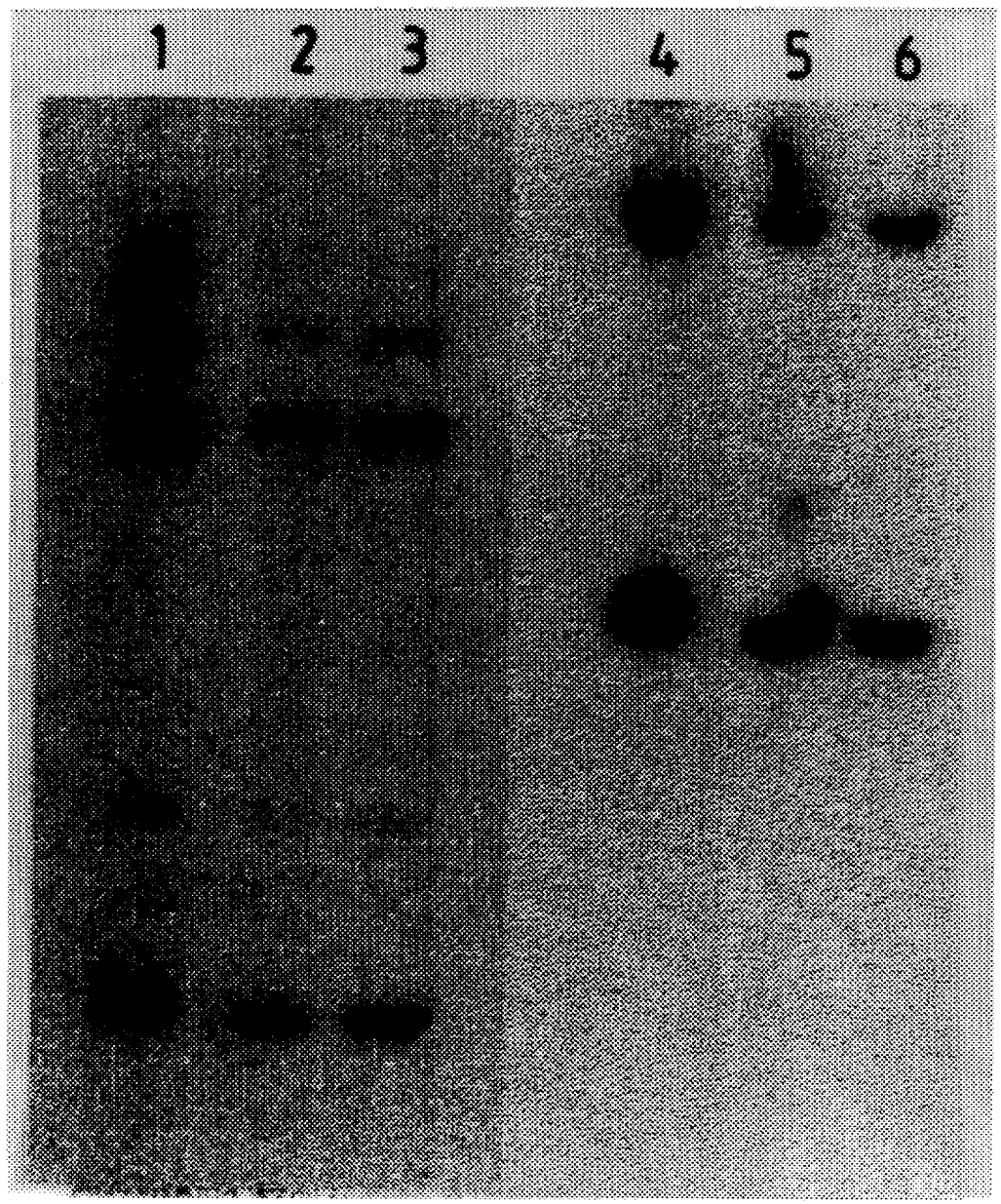
FIG. 7 is a photographic representation showing Southern blot analysis of HEK in cell lines and normal human peripheral blood cell DNA. Samples were digested with Hind III (lanes 1–3) or Bam HI (lanes 4–6), run on a 1% agarose gel and transferred to Zetaprobe membrane. The membrane was hybridised with a 1.1 kb fragment of HEK extending from nucleotides 1,109 to 2,241 (see FIG. 1). Lanes 1 and 4, normal peripheral blood; Lanes 2 and 5, LK63 cells; lanes 3 and 6, LK63/CD20+ cells.

To investigate the basis for overexpression of HEK in the lymphoid tumour cell line LK63, Southern analysis of genomic DNA was performed (FIG. 7). A 1.1 kb fragment covering a less conserved region of HEK (see above), was used as a probe in order to minimise background arising from conserved regions of the catalytic domains of related tyrosine kinase molecules. Compared with normal peripheral blood mononuclear cell DNA, there is no apparent amplification or rearrangement of the HEK gene in the LK63 or LK63/CD20+ tumour cell lines.

Chromosomal assignment of HEK

Figures 8A, 8B:
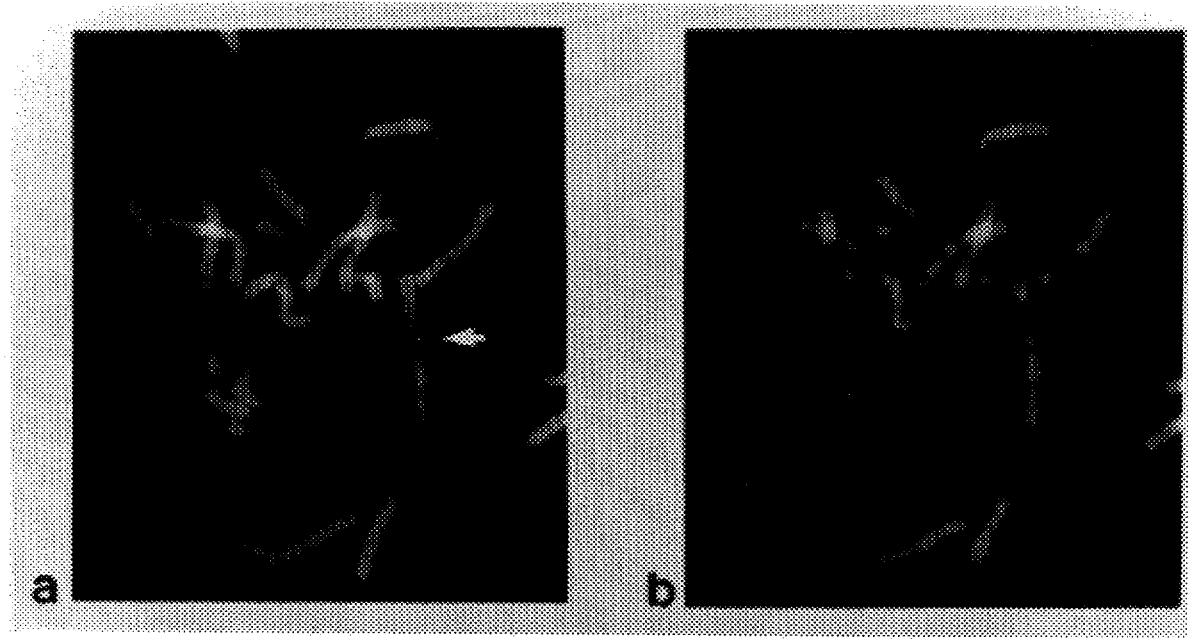
FIGS. 8a–8c are photographic representations showing in situ hybridisation. The ~1.1 kb HEK PCR product referred to above was nick translated with biotin-14-dATP and hybridised in situ at a probe concentration of 5 ng/μl to metaphases from two normal males. Chromosomes were stained before analysis with both propidium iodide (as counterstain) and DAPI (for chromosome identification).
Figure 8C:

HEK cDNA was used as a probe to locate the position of the HEK gene within the normal human chromosome complement. Chromosomal assignment was performed in two ways—by in situ hybridisation and by Southern analysis of somatic cell hybrids. Thirty normal male metaphases were examined for a fluorescent signal: Twenty four of these metaphases showed signal on one or both chromatids of chromosome 3 in the region of 3cen→3p12.1. 85% of this signal was at 3p11.2 (FIG. 8). There were a total of nine non-specific background dots observed in these 30 metaphases. Similar results were obtained from the hybridisation to the second male. Southern blot analysis of the hybrid cell panel showed hybridisation of the HEK probe only to hybrids containing material from human chromosome 3. Bands of 5.2, 4.8, 4.3, 2.4 and 1.9 kb were obtained from the Hind III digest and bands of 4.3, 3.2 and 1.9 kb were obtained from the Taq1 digest. The hybrid cell panel used represents the entire human genome except for chromosomes 2, 6q, 8, 11p and Y. The results from both techniques thus localised the HEK gene to chromosome 3 and in situ hybridisation analysis positioned this more precisely to 3p11.2. This region was not cytogenetically abnormal in HEK-positive tumours. Similarly, there was no isolated change in the copy number of chromosome 3 in HEK-positive cell lines and no isochromosome formation involving chromosome 3.

TABLE 1

Phenotype of HEK-positive human lymphoid cell lines.
The phenotype of HEK-positive cell lines was determined by staining for T and B cell markers followed by FACS analysis. + weakly positive, ++ positive, +++ strongly positive.

|       | ILA4 | IgM | CD19 | CD20 | CD1 | CD2 | CD3 | CD4 | CD7 | CD8 |
|-------|------|-----|------|------|-----|-----|-----|-----|-----|-----|
| LK63  | ++   | +   | +    | −    | −   | −   | −   | −   | −   | −   |
| LK63T | +++  | ++  | ++   | ++   | −   | −   | −   | −   | −   | −   |
| Lila-1| −    | +   | ++   | −    | −   | −   | −   | −   | −   | −   |
| HSB-2 | −    | −   | −    | −    | −   | −   | +   | −   | ++  | −   |
| JM    | +    | −   | −    | −    | +   | −   | +   | ++  | ++  | ++  |
| Molt4 | −    | −   | −    | −    | +   | ++  | −   | −   | ++  | +   |

TABLE 2

Summary of HEK expression in human cell lines
HEK-positive cell lines were characterised using a combination of cell surface staining, Northern blot analysis and Scatchard analysis. + weakly positive, ++ positive, +++ strongly positive. NT, not tested.

| Line   | Lineage  | ILA4/IF | Receptors/cell | RNA |
|--------|----------|---------|----------------|-----|
| LK63   | Pre-B    | ++      | 15,000         | ++  |
| LK63T  | Pre-B    | +++     | NT             | +++ |
| Lila   | Pre-B    | −       | NT             | +   |
| JM     | T cell   | ++      | 9,500          | ++  |
| HSB-2  | T cell   | −       | 1,100          | +   |
| Molt 4 | T cell   | −       | NT             | +   |
| HeLa   | Cervical | −       | NT             | +   |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Ullrich, A. and Schlessigner, J. Cell 61; 203–212,1990.
2. Carpenter, G., & Cohen, S. J. Biol. Chem. 265, 7709–7712, 1990.
3. Williams, L. T. Science 243, 1564–1570, 1989.
4. Yeung, Y. G., Jubinsky, P. T., Sengupta, A., Yeung, D. C. Y., & Stanley, E. R. Proc. Natl. Acad. Sci. USA 84, 1268–1271, 1987.
5. Hanks, S. K., Quinn, A. M. and Hunter, T. Science 241: 42–52,1988.
6. Yarden, Y. and Ullrich, A. Ann. Rev. Biochem. 57: 443–478,1988.
7. Yarden, Y., Kuang, W. J., Yang-Feng, T., Coussens, L., Munemitsu, S., Dull, T. J., Chen, E., Schlessinger, J., Francke, U. & Ullrich, A. EMBO J. 6, 3341–3351, 1987.
8. Chabot, B., Stephenson, D. A., Chapman, V. M., Besner, P. and Verstein, A. Nature 335: 88–89, 1988.
9. Geissler, E. M., Ryan, M. A. and Housman, E. E. Cell 55: 185–192,1988.
10. Nocka, K., Majunder, S., Chabot, B., Rya, P., Cervone, M., Bertstein, A., and Besmer, P. Genes Dev. 3: 816–826, 1989.
11. Williams, D. E., Eisenman, J., Barid, A., Ranch, C., vanNess, K., March. C. J., Park, L. S., Martin, U., Mochinzuki, D. Y., Boswell, H. S., Burgess, G. S., Cosman, D. and Lyman, S. D., Cell 63; 167–174,1990.
12. Zsebo, K. M., Williams, D. A., Geissler, E. N., Broudy, V. C., Martin, F. H., Atkins, H. L., Hsu R. Y., Burkett, N. C., Okino, K. H., Langly, K. E., Smith, K. A., Takeishi, T., Cattanach, B. M., Galli, S. J. and Suggs, S. V. Cell 63: 213–244, 1990.
13. Huang, E., Nocka, K., Beier, D. R., Chui, T. Y., Buck, J., Lahn, H. W., Wellner, D., Leder, P. and Besner, P. Cell 63: 225–233, 1990.
14. Copeland, N. G. Gilbert, D. J., Cho, B. C., Donovan, P. J., Jenkins, N. A., Cosman, D., Anderson, D., Lyman, S. D. and Williams, D. E. Cell 63: 175–183, 1990.
15. Bennett, D. J. Morphol. 98: 199–233,1956.
16. Bishop, J. M. Ann. Rev. Biochem. 52: 301–354, 1983.
17. Hunter, T. and Cooper, J. A. Ann. Rev. Biochem. 54: 897–930,1985.
18. Resh, M. Oncogenes: 1437–1444, 1990.
19. Eiseman, E. and Bolen, J. B. Cancer Cells 2: 303–310, 1990.
20. Veillette, A., Bookman, M. A., Horak, E. M. and Bolen, J. B. Cell 55: 301–308, 1988.
21. Rudd, C. E., Tevillyan, J. M., Dasgupta, J. D., Wong, L. L. and Schlossman, S. F. Pro. Natl. Acad. Sci. USA 85: 5190–5194, 1988.
22. Hirai, H., Maru Y., Hagiwara, K., Nishida, J. and Takaku, F. Science 238: 1717–1720, 1987.
23. Lindberg, R. A. and Hunter, T. Mol. Cell. Biol. 10: 6316–6324,1990.
24. Salvaris, E., Novotny, J. R., Welch, K., Campbell, L. & Boyd, A. W. Leukemia Research (in press).
25. Boyd, A. W., Ward, L. D., Wicks, I. P., Simpson, R. L., Salvaris, E., Wilks, A., Welch, K., Loudovaris, M., Rockman, S. & Busmanis, I. J. Biol. Chem. 267 (5): 3262–3267, 1992.
26. Martin, F. H., Castro, M. M., Aboul-ela, F. & Tinoco, I. Nucleic Acids Res. 13: 8927, 1985.
27. Gearing, D. P., Gough, N. M., King, J. A, Hilton, D. J., Nicola, N. A., Simpson, R. J., Nice, E. C., Kelso, A. & Metcalf, D. EMBO J. 6, 3995–4002, 1987.

28. Wilks, A. *Proc. Natl. Acad. Sci. USA* 86: 1603–1607, 1988.
29. Sanger, F., Nicklen, S. and Coulson, A. R. *Proc. Natl. Acad. Sci. USA* 74: 5463–5467, 1977.
30. Seed, B. & Aruffo, A. *Proc. Natl. Acad. USA* 84, 3365–3369, 1987.
31. van Driel, I., Wilks, A. F., Pietersz, G. A. & Goding, J. W. *Proc. Natl. Acad. Sci. USA* 82: 8619–8623, 1985.
32. Bowtell, D. D. Anal. *Biochem* 162: 463–465. 1987.
33. Trucco, M., & de Petris, S. in *Immunological Methods*, eds. Lefkovits, I., & Pernis, B. (Academic Press, New York, N.Y.) Vol 2, pp 1–26.
34. Lhotak, V., Greer, P., Letwin, K. & Pawson, T. *Mol. Cell. Biol.* 11: 2496–2502, 1991.
35. Singer, S. J., in *Annu. Rev. Cell. Biol.* eds Palade, G. E. Alberts, B. M. and Spudich, J. A. (Annual Reviews Inc. Palo Alto, Calif.), Vol 6: 247–296, 1990.
36. Pasquale, E. B. *Cell Regulation* 2: 523–534, 1991.
37. Cantley, L. C., Auger, K. R., Carpenter, C., Duckworth, B., Graziani, A., Kapellar, R. and Soltoff, S. *Cell* 64, 281–302, 1991.
38. Pearson, R. B., and Kemp, B. E. in Methods in Enzymology, eds. Hunter, T., and Seffon, B. M. (Academic Press, San Diego, La.) Vol 200 p62–81, 1991.
39. Flanagan and Leder *Cell* 63: 185–194, 1990.
40. Kyte and Doolittle *J. Mol. Biol.* 157: 105–132; 1982.

---

We claim:

1. A method of screening for a tissue- or cell-bound ligand to a receptor-type tyrosine kinase having the sequence of SEQ ID NO:10 comprising contacting a fusion protein comprising the extracellular domain of said tyrosine kinase fused to a reporter molecule that produces a detectable signal with the tissue or cell sample to be tested for a time and under conditions whereby said fusion protein binds to said tissue- or cell-bound ligand to form a ligand-fusion protein complex, removing said fusion protein that is not bound to said ligand, and then detecting the signal produced by said reporter molecule in said ligand-fusion protein complex.

2. The method according to claim 1 wherein the reporter molecule is alkaline phosphatase.

3. The method according to claim 1 or 2 wherein said fusion protein is encoded by AP-TAG-HEK.

4. A method of screening for a soluble ligand to a receptor-type tyrosine kinase having the sequence of SEQ ID NO:10 comprising contacting a sample to be tested with a cell line that expresses said tyrosine kinase and screening for phosporylation in said cell line.

5. The method according to claim 4 wherein the cell line is LK63 or a HEK transformant cell line.

6. The method according to claim 4 or 5 wherein the sample is a supernatant fluid.

\* \* \* \* \*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Glu Leu Ile Pro Gln Pro
 1               5
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Glu Leu Ile Pro Gln Pro Ser Asn Glu Val Asn Leu Xaa Asp
 1               5                   10
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Glu Leu Ile Pro Gln Pro Ser Asn Glu Val Asn Leu Xaa Asp Ser Lys
 1               5                   10                  15

Xaa Ile Gln
```

( 2 ) INFORMATION FOR SEQ ID NO:4:

( i ) SEQUENCE CHARACTERISTICS:
        ( A ) LENGTH: 21 amino acids ( B ) TYPE: amino acid
                    ( C ) STRANDEDNESS: single
                    ( D ) TOPOLOGY: linear ( i i ) MOLECULE TYPE: protein ( x i ) SEQUENCE DESCRIPTION: SEQ ID NO:4:

```
Gly  Tyr  Arg  Leu  Pro  Pro  Pro  Met  Asp  Cys  Pro  Ala  Ala  Leu  Tyr  Gln
1              5                        10                       15

Leu  Met  Leu  Asp  Cys
              20
```

( 2 ) INFORMATION FOR SEQ ID NO:5:

( i ) SEQUENCE CHARACTERISTICS:
                    ( A ) LENGTH: 51 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: modified_base
                    ( B ) LOCATION: 6..7
                    ( D ) OTHER INFORMATION: /mod_base=i ( i x ) FEATURE:
                    ( A ) NAME/KEY: modified_base
                    ( B ) LOCATION: 9..10
                    ( D ) OTHER INFORMATION: /mod_base=i ( i x ) FEATURE:
                    ( A ) NAME/KEY: modified_base
                    ( B ) LOCATION: 12..13
                    ( D ) OTHER INFORMATION: /mod_base=i ( i x ) FEATURE:
                    ( A ) NAME/KEY: modified_base
                    ( B ) LOCATION: 15..16
                    ( D ) OTHER INFORMATION: /mod_base=i ( i x ) FEATURE:
                    ( A ) NAME/KEY: modified_base
                    ( B ) LOCATION: 18..19
                    ( D ) OTHER INFORMATION: /mod_base=i ( i x ) FEATURE:
                    ( A ) NAME/KEY: modified_base
                    ( B ) LOCATION: 30..31
                    ( D ) OTHER INFORMATION: /mod_base=i ( i x ) FEATURE:
                    ( A ) NAME/KEY: modified_base
                    ( B ) LOCATION: 33..34
                    ( D ) OTHER INFORMATION: /mod_base=i ( i x ) FEATURE:
                    ( A ) NAME/KEY: modified_base
                    ( B ) LOCATION: 36..37
                    ( D ) OTHER INFORMATION: /mod_base=i ( i x ) FEATURE:
                    ( A ) NAME/KEY: modified_base
                    ( B ) LOCATION: 39..40
                    ( D ) OTHER INFORMATION: /mod_base=i ( i x ) FEATURE:
                    ( A ) NAME/KEY: modified_base
                    ( B ) LOCATION: 48..49
                    ( D ) OTHER INFORMATION: /mod_base=i ( x i ) SEQUENCE DESCRIPTION: SEQ ID NO:5:

TACCGNCTNC CNCCNCCNAT GGACTGCCCN GCNGCNCTNT ACCAACTNAT G          51

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GTAGGGATCC  GAATTCTGCA  CCAGCAACAT  G                                31
```

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GTAGGGATCC  TACACTTGGC  TACTTTCA                                     28
```

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
GCGGATCCTT  GCCTACTTTC  ACCA                                         24
```

( 2 ) INFORMATION FOR SEQ ID NO:9:

( i ) SEQUENCE CHARACTERISTICS:
        ( A ) LENGTH: 3132 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 100..3048

( x i ) SEQUENCE DESCRIPTION: SEQ ID NO:9:

```
CATGGATGGT  AACTTCTCCA  GCAATCAGAG  CGCTCCCCCT  CACATCAGTG  GCATGCTTCA              60

TGGAGATATG  CTCCTCTCAC  TGCCCTCTGC  ACCAGCAAC  ATG GAT TGT CAG CTC                 114
                                               Met Asp Cys Gln Leu
                                                 1               5

TCC ATC CTC CTC CTT CTC AGC TGC TCT GTT CTC GAC AGC TTC GGG GAA                    162
Ser Ile Leu Leu Leu Leu Ser Cys Ser Val Leu Asp Ser Phe Gly Glu
            10                  15                  20

CTG ATT CCG CAG CCT TCC AAT GAA GTC AAT CTA CTG GAT TCA AAA ACA                    210
Leu Ile Pro Gln Pro Ser Asn Glu Val Asn Leu Leu Asp Ser Lys Thr
        25                  30                  35

ATT CAA GGG GAG CTG GGC TGG ATC TCT TAT CCA TCA CAT GGG TGG GAA                    258
Ile Gln Gly Glu Leu Gly Trp Ile Ser Tyr Pro Ser His Gly Trp Glu
    40                  45                  50

GAG ATC AGT GGT GTG GAT GAA CAT TAC ACA CCC ATC AGG ACT TAC CAG                    306
```

-continued

| | Glu | Ile | Ser | Gly | Val | Asp | Glu | His | Tyr | Thr | Pro | Ile | Arg | Thr | Tyr | Gln | |
| --- | --- | --- | --- | --- | --- | --- | --- | --- | --- | --- | --- | --- | --- | --- | --- | --- | --- |
| | | 55 | | | | 60 | | | | | 65 | | | | | | |
| GTG | TGC | AAT | GTC | ATG | GAC | CAC | AGT | CAA | AAC | AAT | TGG | CTG | AGA | ACA | AAC | | 354 |
| Val | Cys | Asn | Val | Met | Asp | His | Ser | Gln | Asn | Asn | Trp | Leu | Arg | Thr | Asn | | |
| 70 | | | | | 75 | | | | | 80 | | | | | 85 | | |
| TGG | GTC | CCC | AGG | AAC | TCA | GCT | CAG | AAG | ATT | TAT | GTG | GAG | CTC | AAG | TTC | | 402 |
| Trp | Val | Pro | Arg | Asn | Ser | Ala | Gln | Lys | Ile | Tyr | Val | Glu | Leu | Lys | Phe | | |
| | | | | 90 | | | | | 95 | | | | | 100 | | | |
| ACT | CTA | CGA | GAC | TGC | AAT | AGC | ATT | CCA | TTG | GTT | TTA | GGA | ACT | TGC | AAG | | 450 |
| Thr | Leu | Arg | Asp | Cys | Asn | Ser | Ile | Pro | Leu | Val | Leu | Gly | Thr | Cys | Lys | | |
| | | | 105 | | | | | 110 | | | | | 115 | | | | |
| GAG | ACA | TTC | AAC | CTG | TAC | TAC | ATG | GAG | TCT | GAT | GAT | GAT | CAT | GGG | GTG | | 498 |
| Glu | Thr | Phe | Asn | Leu | Tyr | Tyr | Met | Glu | Ser | Asp | Asp | Asp | His | Gly | Val | | |
| | | 120 | | | | | 125 | | | | | 130 | | | | | |
| AAA | TTT | CGA | GAG | CAT | CAG | TTT | ACA | AAG | ATT | GAC | ACC | ATT | GCA | GCT | GAT | | 546 |
| Lys | Phe | Arg | Glu | His | Gln | Phe | Thr | Lys | Ile | Asp | Thr | Ile | Ala | Ala | Asp | | |
| | 135 | | | | | 140 | | | | | 145 | | | | | | |
| GAA | AGT | TTC | ACT | CAA | ATG | GAT | CTT | GGG | GAC | CGT | ATT | CTG | AAG | CTC | AAC | | 594 |
| Glu | Ser | Phe | Thr | Gln | Met | Asp | Leu | Gly | Asp | Arg | Ile | Leu | Lys | Leu | Asn | | |
| 150 | | | | | 155 | | | | | 160 | | | | | 165 | | |
| ACT | GAG | ATT | AGA | GAA | GTA | GGT | CCT | GTC | AAC | AAG | AAG | GGA | TTT | TAT | TTG | | 642 |
| Thr | Glu | Ile | Arg | Glu | Val | Gly | Pro | Val | Asn | Lys | Lys | Gly | Phe | Tyr | Leu | | |
| | | | 170 | | | | | 175 | | | | | 180 | | | | |
| GCA | TTT | CAA | GAT | GTT | GGT | GCT | TGT | GTT | GCC | TTG | GTG | TCT | GTG | AGA | GTA | | 690 |
| Ala | Phe | Gln | Asp | Val | Gly | Ala | Cys | Val | Ala | Leu | Val | Ser | Val | Arg | Val | | |
| | | | 185 | | | | | 190 | | | | | 195 | | | | |
| TAC | TTC | AAA | AAG | TGC | CCA | TTT | ACA | GTG | AAG | AAT | CTG | GCT | ATG | TTT | CCA | | 738 |
| Tyr | Phe | Lys | Lys | Cys | Pro | Phe | Thr | Val | Lys | Asn | Leu | Ala | Met | Phe | Pro | | |
| | | 200 | | | | | 205 | | | | | 210 | | | | | |
| GAC | ACG | GTA | CCC | ATG | GAC | TCC | CAG | TCC | CTG | GTG | GAG | GTT | AGA | GGG | TCT | | 786 |
| Asp | Thr | Val | Pro | Met | Asp | Ser | Gln | Ser | Leu | Val | Glu | Val | Arg | Gly | Ser | | |
| | 215 | | | | | 220 | | | | | 225 | | | | | | |
| TGT | GTC | AAC | AAT | TCT | AAG | GAG | GAA | GAT | CCT | CCA | AGG | ATG | TAC | TGC | AGT | | 834 |
| Cys | Val | Asn | Asn | Ser | Lys | Glu | Glu | Asp | Pro | Pro | Arg | Met | Tyr | Cys | Ser | | |
| 230 | | | | | 235 | | | | | 240 | | | | | 245 | | |
| ACA | GAA | GGC | GAA | TGG | CTT | GTA | CCC | ATT | GGC | AAG | TGT | TCC | TGC | AAT | GCT | | 882 |
| Thr | Glu | Gly | Glu | Trp | Leu | Val | Pro | Ile | Gly | Lys | Cys | Ser | Cys | Asn | Ala | | |
| | | | | 250 | | | | | 255 | | | | | 260 | | | |
| GGC | TAT | GAA | GAA | AGA | GGT | TTT | ATG | TGC | CAA | GCT | TGT | CGA | CCA | GGT | TTC | | 930 |
| Gly | Tyr | Glu | Glu | Arg | Gly | Phe | Met | Cys | Gln | Ala | Cys | Arg | Pro | Gly | Phe | | |
| | | | | 265 | | | | | 270 | | | | | 275 | | | |
| TAC | AAG | GCA | TTG | GAT | GGT | AAT | ATG | AAG | TGT | GCT | AAG | TGC | CCG | CCT | CAC | | 978 |
| Tyr | Lys | Ala | Leu | Asp | Gly | Asn | Met | Lys | Cys | Ala | Lys | Cys | Pro | Pro | His | | |
| | | | 280 | | | | | 285 | | | | | 290 | | | | |
| AGT | TCT | ACT | CAG | GAA | GAT | GGT | TCA | ATG | AAC | TGC | AGG | TGT | GAG | AAT | AAT | | 1026 |
| Ser | Ser | Thr | Gln | Glu | Asp | Gly | Ser | Met | Asn | Cys | Arg | Cys | Glu | Asn | Asn | | |
| | 295 | | | | | 300 | | | | | 305 | | | | | | |
| TAC | TTC | CGG | GCA | GAC | AAA | GAC | CCT | CCA | TCC | ATG | GCT | TGT | ACC | CGA | CCT | | 1074 |
| Tyr | Phe | Arg | Ala | Asp | Lys | Asp | Pro | Pro | Ser | Met | Ala | Cys | Thr | Arg | Pro | | |
| 310 | | | | | 315 | | | | | 320 | | | | | 325 | | |
| CCA | TCT | TCA | CCA | AGA | AAT | GTT | ATC | TCT | AAT | ATA | AAC | GAG | ACC | TCA | GTT | | 1122 |
| Pro | Ser | Ser | Pro | Arg | Asn | Val | Ile | Ser | Asn | Ile | Asn | Glu | Thr | Ser | Val | | |
| | | | | 330 | | | | | 335 | | | | | 340 | | | |
| ATC | CTG | GAC | TGG | AGT | TGG | CCC | CTG | GAC | ACA | GGA | GGC | CGG | AAA | GAT | GTT | | 1170 |
| Ile | Leu | Asp | Trp | Ser | Trp | Pro | Leu | Asp | Thr | Gly | Gly | Arg | Lys | Asp | Val | | |
| | | | | 345 | | | | | 350 | | | | | 355 | | | |
| ACC | TTC | AAC | ATC | ATA | TGT | AAA | AAA | TGT | GGG | TGG | AAT | ATA | AAA | CAG | TGT | | 1218 |
| Thr | Phe | Asn | Ile | Ile | Cys | Lys | Lys | Cys | Gly | Trp | Asn | Ile | Lys | Gln | Cys | | |
| | | | 360 | | | | | 365 | | | | | 370 | | | | |
| GAG | CCA | TGC | AGC | CCA | AAT | GTC | CGC | TTC | CTC | CCT | CGA | CAG | TTT | GGA | CTC | | 1266 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Glu | Pro | Cys | Ser | Pro | Asn | Val | Arg | Phe | Leu | Pro | Arg | Gln | Phe | Gly | Leu |      |
|     | 375 |     |     |     | 380 |     |     |     |     | 385 |     |     |     |     |     |      |
| ACC | AAC | ACC | ACG | GTG | ACA | GTG | ACA | GAC | CTT | CTG | GCA | CAT | ACT | AAC | TAC | 1314 |
| Thr | Asn | Thr | Thr | Val | Thr | Val | Thr | Asp | Leu | Leu | Ala | His | Thr | Asn | Tyr |      |
| 390 |     |     |     | 395 |     |     |     |     | 400 |     |     |     |     | 405 |     |      |
| ACC | TTT | GAG | ATT | GAT | GCC | GTT | AAT | GGG | GTG | TCA | GAG | CTG | AGC | TCC | CCA | 1362 |
| Thr | Phe | Glu | Ile | Asp | Ala | Val | Asn | Gly | Val | Ser | Glu | Leu | Ser | Ser | Pro |      |
|     |     |     | 410 |     |     |     |     | 415 |     |     |     |     | 420 |     |     |      |
| CCA | AGA | CAG | TTT | GCT | GCG | GTC | AGC | ATC | ACA | ACT | AAT | CAG | GCT | GCT | CCA | 1410 |
| Pro | Arg | Gln | Phe | Ala | Ala | Val | Ser | Ile | Thr | Thr | Asn | Gln | Ala | Ala | Pro |      |
|     |     | 425 |     |     |     |     | 430 |     |     |     |     | 435 |     |     |     |      |
| TCA | CCT | GTC | CTG | ACG | ATT | AAG | AAA | GAT | CGG | ACC | TCC | AGA | AAT | AGC | ATC | 1458 |
| Ser | Pro | Val | Leu | Thr | Ile | Lys | Lys | Asp | Arg | Thr | Ser | Arg | Asn | Ser | Ile |      |
|     | 440 |     |     |     |     | 445 |     |     |     |     | 450 |     |     |     |     |      |
| TCT | TTG | TCC | TGG | CAA | GAA | CCT | GAA | CAT | CCT | AAT | GGG | ATC | ATA | TTG | GAC | 1506 |
| Ser | Leu | Ser | Trp | Gln | Glu | Pro | Glu | His | Pro | Asn | Gly | Ile | Ile | Leu | Asp |      |
|     | 455 |     |     |     | 460 |     |     |     |     | 465 |     |     |     |     |     |      |
| TAC | GAG | GTC | AAA | TAC | TAT | GAA | AAG | CAG | GAA | CAA | GAA | ACA | AGT | TAT | ACC | 1554 |
| Tyr | Glu | Val | Lys | Tyr | Tyr | Glu | Lys | Gln | Glu | Gln | Glu | Thr | Ser | Tyr | Thr |      |
| 470 |     |     |     | 475 |     |     |     |     | 480 |     |     |     |     | 485 |     |      |
| ATT | CTG | AGG | GCA | AGA | GGC | ACA | AAT | GTT | ACC | ATC | AGT | AGC | CTC | AAG | CCT | 1602 |
| Ile | Leu | Arg | Ala | Arg | Gly | Thr | Asn | Val | Thr | Ile | Ser | Ser | Leu | Lys | Pro |      |
|     |     |     |     | 490 |     |     |     |     | 495 |     |     |     |     | 500 |     |      |
| GAC | ACT | ATA | TAC | GTA | TTA | CAA | ATC | CGA | GCC | CGA | ACA | GCC | GCT | GGA | TAT | 1650 |
| Asp | Thr | Ile | Tyr | Val | Leu | Gln | Ile | Arg | Ala | Arg | Thr | Ala | Ala | Gly | Tyr |      |
|     |     |     | 505 |     |     |     |     | 510 |     |     |     |     | 515 |     |     |      |
| GGG | ACG | AAC | AGC | CGC | AAG | TTT | GAG | TTT | GAA | ACT | AGT | CCA | GAC | TCT | TTC | 1698 |
| Gly | Thr | Asn | Ser | Arg | Lys | Phe | Glu | Phe | Glu | Thr | Ser | Pro | Asp | Ser | Phe |      |
|     |     | 520 |     |     |     |     | 525 |     |     |     |     | 530 |     |     |     |      |
| TCC | ATC | TCT | GGT | GAA | AGT | AGC | CAA | GTG | GTC | ATG | ATC | GCC | ATT | TCA | GCG | 1746 |
| Ser | Ile | Ser | Gly | Glu | Ser | Ser | Gln | Val | Val | Met | Ile | Ala | Ile | Ser | Ala |      |
|     | 535 |     |     |     |     | 540 |     |     |     |     | 545 |     |     |     |     |      |
| GCA | GTA | GCA | ATT | ATT | CTC | CTC | ACT | GTT | GTC | ATC | TAT | GTT | TTG | ATT | GGG | 1794 |
| Ala | Val | Ala | Ile | Ile | Leu | Leu | Thr | Val | Val | Ile | Tyr | Val | Leu | Ile | Gly |      |
| 550 |     |     |     |     | 555 |     |     |     |     | 560 |     |     |     |     | 565 |      |
| AGG | TTC | TGT | GGC | TAT | AAG | TCA | AAA | CAT | GGG | GCA | GAT | GAA | AAA | AGA | CTT | 1842 |
| Arg | Phe | Cys | Gly | Tyr | Lys | Ser | Lys | His | Gly | Ala | Asp | Glu | Lys | Arg | Leu |      |
|     |     |     |     | 570 |     |     |     |     | 575 |     |     |     |     | 580 |     |      |
| CAT | TTT | GGC | AAT | GGG | CAT | TTA | AAA | CTT | CCA | GGT | CTC | AGG | ACT | TAT | GTT | 1890 |
| His | Phe | Gly | Asn | Gly | His | Leu | Lys | Leu | Pro | Gly | Leu | Arg | Thr | Tyr | Val |      |
|     |     |     | 585 |     |     |     |     | 590 |     |     |     |     | 595 |     |     |      |
| GAC | CCA | CAT | ACA | TAT | GAA | GAC | CCT | ACC | CAA | GCT | GTT | CAT | GAG | TTT | GCC | 1938 |
| Asp | Pro | His | Thr | Tyr | Glu | Asp | Pro | Thr | Gln | Ala | Val | His | Glu | Phe | Ala |      |
|     |     | 600 |     |     |     |     | 605 |     |     |     |     | 610 |     |     |     |      |
| AAG | GAA | TTG | GAT | GCC | ACC | AAC | ATA | TCC | ATT | GAT | AAA | GTT | GTT | GGA | GCA | 1986 |
| Lys | Glu | Leu | Asp | Ala | Thr | Asn | Ile | Ser | Ile | Asp | Lys | Val | Val | Gly | Ala |      |
|     | 615 |     |     |     |     | 620 |     |     |     |     | 625 |     |     |     |     |      |
| GGT | GAA | TTT | GGA | GAG | GTG | TGC | AGT | GGT | CGC | TTA | AAA | CTT | CCT | TCA | AAA | 2034 |
| Gly | Glu | Phe | Gly | Glu | Val | Cys | Ser | Gly | Arg | Leu | Lys | Leu | Pro | Ser | Lys |      |
| 630 |     |     |     |     | 635 |     |     |     |     | 640 |     |     |     |     | 645 |      |
| AAA | GAG | ATT | TCA | GTG | GCC | ATT | AAA | ACC | CTG | AAA | GTT | GGC | TAC | ACA | GAA | 2082 |
| Lys | Glu | Ile | Ser | Val | Ala | Ile | Lys | Thr | Leu | Lys | Val | Gly | Tyr | Thr | Glu |      |
|     |     |     |     | 650 |     |     |     |     | 655 |     |     |     |     | 660 |     |      |
| AAG | CAG | AGG | AGA | GAC | TTC | CTG | GGA | GAA | GCA | AGC | ATT | ATG | GGA | CAG | TTT | 2130 |
| Lys | Gln | Arg | Arg | Asp | Phe | Leu | Gly | Glu | Ala | Ser | Ile | Met | Gly | Gln | Phe |      |
|     |     |     | 665 |     |     |     |     | 670 |     |     |     |     | 675 |     |     |      |
| GAC | CAC | CCC | AAT | ATC | ATT | CGA | CTG | GAA | GGA | GTT | GTT | ACC | AAA | AGT | AAG | 2178 |
| Asp | His | Pro | Asn | Ile | Ile | Arg | Leu | Glu | Gly | Val | Val | Thr | Lys | Ser | Lys |      |
|     |     | 680 |     |     |     |     | 685 |     |     |     |     | 690 |     |     |     |      |
| CCA | GTT | ATG | ATT | GTC | ACA | GAA | TAC | ATG | GAG | AAT | GGT | TCC | TTG | GAT | AGT | 2226 |

|  |  |  |  |  |  |  |  |  |  |  |  |  |  |  |  |
|---|---|---|---|---|---|---|---|---|---|---|---|---|---|---|---|
| Pro | Val | Met | Ile | Val | Thr | Glu | Tyr | Met | Glu | Asn | Gly | Ser | Leu | Asp | Ser |
|  | 695 |  |  |  | 700 |  |  |  |  | 705 |  |  |  |  |  |

| TTC | CTA | CGT | AAA | CAC | GAT | GCC | CAG | TTT | ACT | GTC | ATT | CAG | CTA | CTG | GGG | 2274 |
|---|---|---|---|---|---|---|---|---|---|---|---|---|---|---|---|---|
| Phe | Leu | Arg | Lys | His | Asp | Ala | Gln | Phe | Thr | Val | Ile | Gln | Leu | Leu | Gly |  |
| 710 |  |  |  |  | 715 |  |  |  |  | 720 |  |  |  |  | 725 |  |

| ATG | CTT | CGA | GGG | ATA | GCA | TCT | GGC | ATG | AAG | TAC | CTG | TCA | GAC | ATG | GGC | 2322 |
|---|---|---|---|---|---|---|---|---|---|---|---|---|---|---|---|---|
| Met | Leu | Arg | Gly | Ile | Ala | Ser | Gly | Met | Lys | Tyr | Leu | Ser | Asp | Met | Gly |  |
|  |  |  |  | 730 |  |  |  |  | 735 |  |  |  |  | 740 |  |  |

| TAT | GTT | CAC | CGA | GAC | CTC | GCT | GCT | CGG | AAC | ATC | TTG | ATC | AAC | AGT | AAC | 2370 |
|---|---|---|---|---|---|---|---|---|---|---|---|---|---|---|---|---|
| Tyr | Val | His | Arg | Asp | Leu | Ala | Ala | Arg | Asn | Ile | Leu | Ile | Asn | Ser | Asn |  |
|  |  |  | 745 |  |  |  |  | 750 |  |  |  |  | 755 |  |  |  |

| TTG | GTG | TGT | AAG | GTT | TCT | GAT | TTC | GGA | CTT | TCG | CGT | GTC | CTG | GAG | GAT | 2418 |
|---|---|---|---|---|---|---|---|---|---|---|---|---|---|---|---|---|
| Leu | Val | Cys | Lys | Val | Ser | Asp | Phe | Gly | Leu | Ser | Arg | Val | Leu | Glu | Asp |  |
|  |  | 760 |  |  |  |  | 765 |  |  |  |  | 770 |  |  |  |  |

| GAC | CCA | GAA | GCT | GCT | TAT | ACA | ACA | AGA | GGA | GGG | AAG | ATC | CCA | ATC | AGG | 2466 |
|---|---|---|---|---|---|---|---|---|---|---|---|---|---|---|---|---|
| Asp | Pro | Glu | Ala | Ala | Tyr | Thr | Thr | Arg | Gly | Gly | Lys | Ile | Pro | Ile | Arg |  |
| 775 |  |  |  |  | 780 |  |  |  |  | 785 |  |  |  |  |  |  |

| TGG | ACA | TCA | CCA | GAA | GCT | ATA | GCC | TAC | CGC | AAG | TTC | ACG | TCA | GCC | AGC | 2514 |
|---|---|---|---|---|---|---|---|---|---|---|---|---|---|---|---|---|
| Trp | Thr | Ser | Pro | Glu | Ala | Ile | Ala | Tyr | Arg | Lys | Phe | Thr | Ser | Ala | Ser |  |
| 790 |  |  |  |  | 795 |  |  |  |  | 800 |  |  |  |  | 805 |  |

| GAT | GTA | TGG | AGT | TAT | GGG | ATT | GTT | CTC | TGG | GAG | GTG | ATG | TCT | TAT | GGA | 2562 |
|---|---|---|---|---|---|---|---|---|---|---|---|---|---|---|---|---|
| Asp | Val | Trp | Ser | Tyr | Gly | Ile | Val | Leu | Trp | Glu | Val | Met | Ser | Tyr | Gly |  |
|  |  |  |  | 810 |  |  |  |  | 815 |  |  |  |  | 820 |  |  |

| GAG | AGA | CCA | TAC | TGG | GAG | ATG | TCC | AAT | CAG | GAT | GTA | ATT | AAA | GCT | GTA | 2610 |
|---|---|---|---|---|---|---|---|---|---|---|---|---|---|---|---|---|
| Glu | Arg | Pro | Tyr | Trp | Glu | Met | Ser | Asn | Gln | Asp | Val | Ile | Lys | Ala | Val |  |
|  |  | 825 |  |  |  |  | 830 |  |  |  |  | 835 |  |  |  |  |

| GAT | GAG | GGC | TAT | CGA | CTG | CCA | CCC | CCC | ATG | GAC | TGC | CCA | GCT | GCC | TTG | 2658 |
|---|---|---|---|---|---|---|---|---|---|---|---|---|---|---|---|---|
| Asp | Glu | Gly | Tyr | Arg | Leu | Pro | Pro | Pro | Met | Asp | Cys | Pro | Ala | Ala | Leu |  |
|  |  | 840 |  |  |  |  | 845 |  |  |  |  | 850 |  |  |  |  |

| TAT | CAG | CTG | ATG | CTG | GAC | TGC | TGG | CAG | AAA | GAC | AGG | AAC | AAC | AGA | CCC | 2706 |
|---|---|---|---|---|---|---|---|---|---|---|---|---|---|---|---|---|
| Tyr | Gln | Leu | Met | Leu | Asp | Cys | Trp | Gln | Lys | Asp | Arg | Asn | Asn | Arg | Pro |  |
| 855 |  |  |  |  | 860 |  |  |  |  | 865 |  |  |  |  |  |  |

| AAG | TTT | GAG | CAG | ATT | GTT | AGT | ATT | CTG | GAC | AAG | CTT | ATC | CGG | AAT | CCC | 2754 |
|---|---|---|---|---|---|---|---|---|---|---|---|---|---|---|---|---|
| Lys | Phe | Glu | Gln | Ile | Val | Ser | Ile | Leu | Asp | Lys | Leu | Ile | Arg | Asn | Pro |  |
| 870 |  |  |  |  | 875 |  |  |  |  | 880 |  |  |  |  | 885 |  |

| GGC | AGC | CTG | AAG | ATC | ATC | ACC | AGT | GCA | GCC | GCA | AGG | CCA | TCA | AAC | CTT | 2802 |
|---|---|---|---|---|---|---|---|---|---|---|---|---|---|---|---|---|
| Gly | Ser | Leu | Lys | Ile | Ile | Thr | Ser | Ala | Ala | Ala | Arg | Pro | Ser | Asn | Leu |  |
|  |  |  |  | 890 |  |  |  |  | 895 |  |  |  |  | 900 |  |  |

| CTT | CTG | GAC | CAA | AGC | AAT | GTG | GAT | ATC | TCT | ACC | TTC | CGC | ACA | ACA | GGT | 2850 |
|---|---|---|---|---|---|---|---|---|---|---|---|---|---|---|---|---|
| Leu | Leu | Asp | Gln | Ser | Asn | Val | Asp | Ile | Ser | Thr | Phe | Arg | Thr | Thr | Gly |  |
|  |  |  | 905 |  |  |  |  | 910 |  |  |  |  | 915 |  |  |  |

| GAC | TGG | CTT | AAT | GGT | GTC | CGG | ACA | GCA | CAC | TGC | AAG | GAA | ATC | TTC | ACG | 2898 |
|---|---|---|---|---|---|---|---|---|---|---|---|---|---|---|---|---|
| Asp | Trp | Leu | Asn | Gly | Val | Arg | Thr | Ala | His | Cys | Lys | Glu | Ile | Phe | Thr |  |
|  |  | 920 |  |  |  |  | 925 |  |  |  |  | 930 |  |  |  |  |

| GGC | GTG | GAG | TAC | AGT | TCT | TGT | GAC | ACA | ATA | GCC | AAG | ATT | TCC | ACA | GAT | 2946 |
|---|---|---|---|---|---|---|---|---|---|---|---|---|---|---|---|---|
| Gly | Val | Glu | Tyr | Ser | Ser | Cys | Asp | Thr | Ile | Ala | Lys | Ile | Ser | Thr | Asp |  |
|  | 935 |  |  |  |  | 940 |  |  |  |  | 945 |  |  |  |  |  |

| GAC | ATG | AAA | AAG | GTT | GGT | GTC | ACC | GTG | GTT | GGG | CCA | CAG | AAG | AAG | ATC | 2994 |
|---|---|---|---|---|---|---|---|---|---|---|---|---|---|---|---|---|
| Asp | Met | Lys | Lys | Val | Gly | Val | Thr | Val | Val | Gly | Pro | Gln | Lys | Lys | Ile |  |
| 950 |  |  |  | 955 |  |  |  |  | 960 |  |  |  |  | 965 |  |  |

| ATC | AGT | AGC | ATT | AAA | GCT | CTA | GAA | ACG | CAA | TCA | AAG | AAT | GGC | CCA | GTT | 3042 |
|---|---|---|---|---|---|---|---|---|---|---|---|---|---|---|---|---|
| Ile | Ser | Ser | Ile | Lys | Ala | Leu | Glu | Thr | Gln | Ser | Lys | Asn | Gly | Pro | Val |  |
|  |  |  |  | 970 |  |  |  |  | 975 |  |  |  |  | 980 |  |  |

| CCC | GTG | TAAAGCACGA | CGGAAGTGCT | TCTGGACGGA | AGTGGTGGCT | GTGGAAGGCG | 3098 |
|---|---|---|---|---|---|---|---|
| Pro | Val |  |  |  |  |  |  |

| TCAAGTCATC | CTGCAGACAG | ACAATAATTC | TGGA | 3132 |
|---|---|---|---|---|

( 2 ) INFORMATION FOR SEQ ID NO:10:

( i ) SEQUENCE CHARACTERISTICS:

(A) LENGTH: 983 amino acids
(B) TYPE: amino acid
(D) TOPOLOGY: linear (ii) MOLECULE TYPE: protein (xi) SEQUENCE DESCRIPTION: SEQ ID NO:10:

| Met | Asp | Cys | Gln | Leu | Ser | Ile | Leu | Leu | Leu | Ser | Cys | Ser | Val | Leu |
|---|---|---|---|---|---|---|---|---|---|---|---|---|---|---|
| 1 | | | | 5 | | | | | 10 | | | | | 15 |

| Asp | Ser | Phe | Gly | Glu | Leu | Ile | Pro | Gln | Pro | Ser | Asn | Glu | Val | Asn | Leu |
|---|---|---|---|---|---|---|---|---|---|---|---|---|---|---|---|
| | | | 20 | | | | | 25 | | | | | 30 | | |

| Leu | Asp | Ser | Lys | Thr | Ile | Gln | Gly | Glu | Leu | Gly | Trp | Ile | Ser | Tyr | Pro |
|---|---|---|---|---|---|---|---|---|---|---|---|---|---|---|---|
| | | | 35 | | | | 40 | | | | | 45 | | | |

| Ser | His | Gly | Trp | Glu | Glu | Ile | Ser | Gly | Val | Asp | Glu | His | Tyr | Thr | Pro |
|---|---|---|---|---|---|---|---|---|---|---|---|---|---|---|---|
| | 50 | | | | | 55 | | | | | 60 | | | | |

| Ile | Arg | Thr | Tyr | Gln | Val | Cys | Asn | Val | Met | Asp | His | Ser | Gln | Asn | Asn |
|---|---|---|---|---|---|---|---|---|---|---|---|---|---|---|---|
| 65 | | | | | 70 | | | | | 75 | | | | | 80 |

| Trp | Leu | Arg | Thr | Asn | Trp | Val | Pro | Arg | Asn | Ser | Ala | Gln | Lys | Ile | Tyr |
|---|---|---|---|---|---|---|---|---|---|---|---|---|---|---|---|
| | | | | 85 | | | | | 90 | | | | | 95 | |

| Val | Glu | Leu | Lys | Phe | Thr | Leu | Arg | Asp | Cys | Asn | Ser | Ile | Pro | Leu | Val |
|---|---|---|---|---|---|---|---|---|---|---|---|---|---|---|---|
| | | | 100 | | | | | 105 | | | | | 110 | | |

| Leu | Gly | Thr | Cys | Lys | Glu | Thr | Phe | Asn | Leu | Tyr | Tyr | Met | Glu | Ser | Asp |
|---|---|---|---|---|---|---|---|---|---|---|---|---|---|---|---|
| | | | 115 | | | | | 120 | | | | | 125 | | |

| Asp | Asp | His | Gly | Val | Lys | Phe | Arg | Glu | His | Gln | Phe | Thr | Lys | Ile | Asp |
|---|---|---|---|---|---|---|---|---|---|---|---|---|---|---|---|
| | 130 | | | | | 135 | | | | | 140 | | | | |

| Thr | Ile | Ala | Ala | Asp | Glu | Ser | Phe | Thr | Gln | Met | Asp | Leu | Gly | Asp | Arg |
|---|---|---|---|---|---|---|---|---|---|---|---|---|---|---|---|
| 145 | | | | | 150 | | | | | 155 | | | | | 160 |

| Ile | Leu | Lys | Leu | Asn | Thr | Glu | Ile | Arg | Glu | Val | Gly | Pro | Val | Asn | Lys |
|---|---|---|---|---|---|---|---|---|---|---|---|---|---|---|---|
| | | | | 165 | | | | | 170 | | | | | 175 | |

| Lys | Gly | Phe | Tyr | Leu | Ala | Phe | Gln | Asp | Val | Gly | Ala | Cys | Val | Ala | Leu |
|---|---|---|---|---|---|---|---|---|---|---|---|---|---|---|---|
| | | | 180 | | | | | 185 | | | | | 190 | | |

| Val | Ser | Val | Arg | Val | Tyr | Phe | Lys | Lys | Cys | Pro | Phe | Thr | Val | Lys | Asn |
|---|---|---|---|---|---|---|---|---|---|---|---|---|---|---|---|
| | | 195 | | | | | 200 | | | | | 205 | | | |

| Leu | Ala | Met | Phe | Pro | Asp | Thr | Val | Pro | Met | Asp | Ser | Gln | Ser | Leu | Val |
|---|---|---|---|---|---|---|---|---|---|---|---|---|---|---|---|
| | 210 | | | | | 215 | | | | | 220 | | | | |

| Glu | Val | Arg | Gly | Ser | Cys | Val | Asn | Asn | Ser | Lys | Glu | Glu | Asp | Pro | Pro |
|---|---|---|---|---|---|---|---|---|---|---|---|---|---|---|---|
| 225 | | | | | 230 | | | | | 235 | | | | | 240 |

| Arg | Met | Tyr | Cys | Ser | Thr | Glu | Gly | Glu | Trp | Leu | Val | Pro | Ile | Gly | Lys |
|---|---|---|---|---|---|---|---|---|---|---|---|---|---|---|---|
| | | | | 245 | | | | | 250 | | | | | 255 | |

| Cys | Ser | Cys | Asn | Ala | Gly | Tyr | Glu | Glu | Arg | Gly | Phe | Met | Cys | Gln | Ala |
|---|---|---|---|---|---|---|---|---|---|---|---|---|---|---|---|
| | | | 260 | | | | | 265 | | | | | 270 | | |

| Cys | Arg | Pro | Gly | Phe | Tyr | Lys | Ala | Leu | Asp | Gly | Asn | Met | Lys | Cys | Ala |
|---|---|---|---|---|---|---|---|---|---|---|---|---|---|---|---|
| | | 275 | | | | | 280 | | | | | 285 | | | |

| Lys | Cys | Pro | Pro | His | Ser | Ser | Thr | Gln | Glu | Asp | Gly | Ser | Met | Asn | Cys |
|---|---|---|---|---|---|---|---|---|---|---|---|---|---|---|---|
| | 290 | | | | | 295 | | | | | 300 | | | | |

| Arg | Cys | Glu | Asn | Asn | Tyr | Phe | Arg | Ala | Asp | Lys | Asp | Pro | Pro | Ser | Met |
|---|---|---|---|---|---|---|---|---|---|---|---|---|---|---|---|
| 305 | | | | | 310 | | | | | 315 | | | | | 320 |

| Ala | Cys | Thr | Arg | Pro | Pro | Ser | Ser | Pro | Arg | Asn | Val | Ile | Ser | Asn | Ile |
|---|---|---|---|---|---|---|---|---|---|---|---|---|---|---|---|
| | | | | 325 | | | | | 330 | | | | | 335 | |

| Asn | Glu | Thr | Ser | Val | Ile | Leu | Asp | Trp | Ser | Trp | Pro | Leu | Asp | Thr | Gly |
|---|---|---|---|---|---|---|---|---|---|---|---|---|---|---|---|
| | | | 340 | | | | | 345 | | | | | 350 | | |

| Gly | Arg | Lys | Asp | Val | Thr | Phe | Asn | Ile | Ile | Cys | Lys | Lys | Cys | Gly | Trp |
|---|---|---|---|---|---|---|---|---|---|---|---|---|---|---|---|
| | | 355 | | | | | 360 | | | | | 365 | | | |

| Asn | Ile | Lys | Gln | Cys | Glu | Pro | Cys | Ser | Pro | Asn | Val | Arg | Phe | Leu | Pro |
|---|---|---|---|---|---|---|---|---|---|---|---|---|---|---|---|
| 370 | | | | | 375 | | | | | 380 | | | | | |

| Arg 385 | Gln | Phe | Gly | Leu | Thr 390 | Asn | Thr | Thr | Val 395 | Thr | Val | Thr | Asp | Leu | Leu 400 |

Ala His Thr Asn Tyr Thr Phe Glu Ile Asp Ala Val Asn Gly Val Ser
                     405              410              415

Glu Leu Ser Ser Pro Pro Arg Gln Phe Ala Ala Val Ser Ile Thr Thr
             420              425              430

Asn Gln Ala Ala Pro Ser Pro Val Leu Thr Ile Lys Lys Asp Arg Thr
         435              440              445

Ser Arg Asn Ser Ile Ser Leu Ser Trp Gln Glu Pro Glu His Pro Asn
     450              455              460

Gly Ile Ile Leu Asp Tyr Glu Val Lys Tyr Tyr Glu Lys Gln Glu Gln
465              470              475                       480

Glu Thr Ser Tyr Thr Ile Leu Arg Ala Arg Gly Thr Asn Val Thr Ile
                 485              490              495

Ser Ser Leu Lys Pro Asp Thr Ile Tyr Val Leu Gln Ile Arg Ala Arg
             500              505              510

Thr Ala Ala Gly Tyr Gly Thr Asn Ser Arg Lys Phe Glu Phe Glu Thr
         515              520              525

Ser Pro Asp Ser Phe Ser Ile Ser Gly Glu Ser Ser Gln Val Val Met
     530              535              540

Ile Ala Ile Ser Ala Ala Val Ala Ile Ile Leu Leu Thr Val Val Ile
545              550              555                       560

Tyr Val Leu Ile Gly Arg Phe Cys Gly Tyr Lys Ser Lys His Gly Ala
                 565              570              575

Asp Glu Lys Arg Leu His Phe Gly Asn Gly His Leu Lys Leu Pro Gly
             580              585              590

Leu Arg Thr Tyr Val Asp Pro His Thr Tyr Glu Asp Pro Thr Gln Ala
     595              600              605

Val His Glu Phe Ala Lys Glu Leu Asp Ala Thr Asn Ile Ser Ile Asp
     610              615              620

Lys Val Val Gly Ala Gly Glu Phe Gly Glu Val Cys Ser Gly Arg Leu
625              630              635                       640

Lys Leu Pro Ser Lys Lys Glu Ile Ser Val Ala Ile Lys Thr Leu Lys
             645              650              655

Val Gly Tyr Thr Glu Lys Gln Arg Arg Asp Phe Leu Gly Glu Ala Ser
             660              665              670

Ile Met Gly Gln Phe Asp His Pro Asn Ile Ile Arg Leu Glu Gly Val
         675              680              685

Val Thr Lys Ser Lys Pro Val Met Ile Val Thr Glu Tyr Met Glu Asn
     690              695              700

Gly Ser Leu Asp Ser Phe Leu Arg Lys His Asp Ala Gln Phe Thr Val
705              710              715              720

Ile Gln Leu Leu Gly Met Leu Arg Gly Ile Ala Ser Gly Met Lys Tyr
             725              730              735

Leu Ser Asp Met Gly Tyr Val His Arg Asp Leu Ala Ala Arg Asn Ile
         740              745              750

Leu Ile Asn Ser Asn Leu Val Cys Lys Val Ser Asp Phe Gly Leu Ser
         755              760              765

Arg Val Leu Glu Asp Asp Pro Glu Ala Ala Tyr Thr Thr Arg Gly Gly
     770              775              780

Lys Ile Pro Ile Arg Trp Thr Ser Pro Glu Ala Ile Ala Tyr Arg Lys
785              790              795                       800

Phe Thr Ser Ala Ser Asp Val Trp Ser Tyr Gly Ile Val Leu Trp Glu
             805              810              815

5,674,691

31

32

-continued

| Val | Met | Ser | Tyr 820 | Gly | Glu | Arg | Pro | Tyr 825 | Trp | Glu | Met | Ser | Asn 830 | Gln | Asp |
| Val | Ile | Lys 835 | Ala | Val | Asp | Glu | Gly 840 | Tyr | Arg | Leu | Pro | Pro 845 | Met | Asp |
| Cys | Pro 850 | Ala | Ala | Leu | Tyr | Gln 855 | Leu | Met | Leu | Asp | Cys 860 | Trp | Gln | Lys | Asp |
| Arg 865 | Asn | Asn | Arg | Pro | Lys 870 | Phe | Glu | Gln | Ile | Val 875 | Ser | Ile | Leu | Asp | Lys 880 |
| Leu | Ile | Arg | Asn | Pro 885 | Gly | Ser | Leu | Lys | Ile 890 | Ile | Thr | Ser | Ala | Ala 895 | Ala |
| Arg | Pro | Ser | Asn 900 | Leu | Leu | Leu | Asp | Gln 905 | Ser | Asn | Val | Asp | Ile 910 | Ser | Thr |
| Phe | Arg | Thr 915 | Thr | Gly | Asp | Trp | Leu 920 | Asn | Gly | Val | Arg | Thr 925 | Ala | His | Cys |
| Lys | Glu 930 | Ile | Phe | Thr | Gly | Val 935 | Glu | Tyr | Ser | Ser | Cys 940 | Asp | Thr | Ile | Ala |
| Lys 945 | Ile | Ser | Thr | Asp | Asp 950 | Met | Lys | Lys | Val | Gly 955 | Val | Thr | Val | Val | Gly 960 |
| Pro | Gln | Lys | Lys | Ile 965 | Ile | Ser | Ser | Ile | Lys 970 | Ala | Leu | Glu | Thr | Gln 975 | Ser |
| Lys | Asn | Gly | Pro 980 | Val | Pro | Val | | | | | | | | | |

( 2 ) INFORMATION FOR SEQ ID NO:11:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

| Met 1 | Ala | Leu | Leu | Phe 5 | Leu | Ala | Ala | Val | Ala 10 | Ala | Met | Glu | Thr | Met 15 | Thr |
| Arg | Ala | Thr | Ala 20 | Thr | Ala | Asn | Ala | Ser 25 | Val | Tyr | Tyr | Thr | Ser 30 | Val | Ile |
| Ala | Thr | Lys 35 | Ser | Ala | Phe | Trp | Ser 40 | Ala | Pro | Tyr | Leu | Val 45 | Ser | Val | Phe |
| Gly | Leu 50 | Met | Val | Val | Ser | Phe 55 | Leu | Thr | Arg | Ala | Glu 60 | Val | Val | Ile | Lys |
| Leu 65 | Asn | Gly | Asp | Met | Arg 70 | Thr | Lys | Pro | Asn | Ser 75 | Val | Ala | Lys | Pro | Ala 80 |
| Thr | Phe | Ser | Gln | Glu 85 | Ala | Glu | Gly | Ser | His 90 | Ser | Asn | Asn | Leu | Asn 95 | Thr |
| Phe | Glu | Pro | Asn 100 | Leu | Thr | Phe | Ile | Asn 105 | Arg | Gly | His | Arg | Thr 110 | Met | Arg |
| Val | Ser | Leu 115 | Asn | Pro | Ser | Asn | Tyr 120 | Met | Ser | Leu | Phe | Ser 125 | Ile | Gln | Phe |
| Val | Glu 130 | Met | Thr | Gly | Ala | Glu 135 | Thr | Ile | Ala | Thr | Ile 140 | Pro | Arg | Ser | Pro |
| Ser 145 | Glu | Ala | Pro | Ile | Thr 150 | Arg | Thr | Gly | Tyr | Phe 155 | Glu | Val | Ser | Val | Gly 160 |
| | Ile | Val | Ile | Glu | His 165 | Pro | Arg | Glu | Asp | Tyr 170 | Arg | Ala | Asp | Arg 175 | Ser |

```
Ser  Arg  Asp  Asp  Glu  Val  Leu  Glu  Cys  Arg  Ser  Ile  Ser  Ser  Trp  Pro
          180                      185                     190

Asp  Gln  Ile  Ile  Arg  Glu  His  Asn  Phe  Asn  Ser  Ser  Met  Ala  Ser  Gln
          195                      200                     205

Thr  Asn  Thr  Ala  Arg  Asp  Gly  Arg  Gly  Met  Val  Val  Val  Val  Lys  Phe
          210                      215                     220

Gly  Met  Cys  Gln  Leu  Thr  Asp  Asp  Tyr  Lys  Met  Lys  Ile  Ile  Phe  Asn
225                           230                     235                     240

Glu  Arg  Ile  Val  Ser  Phe  Val  Lys  Glu  Ile  Tyr  Lys  Gly  Arg  Tyr
                    245                      250                     255

Ser  Lys  Pro  Phe  Pro  His  Val  Ser  Asn  Thr  Pro  Ile  Met  His  Gln  Val
          260                      265                     270

Ser  Ala  Thr  Met  Arg  Thr  Pro  Gln  Gln  Glu  Leu  Arg  Glu  Leu  Pro  Leu
          275                      280                     285

Gly  Ala  Gly  Val  Val  Phe  Val  Val  Ser  Leu  Ala  Ser  Ile  Val  Cys  Ser
     290                      295                     300

Lys  Arg  Ala  Ser  Lys  Glu  Ala  Val  Tyr  Ser  Asp  Leu  Gln  Tyr  Ser  Thr
305                 310                      315                     320

Arg  Gly  Ser  Ala  Ser  Arg  Ile  Phe  Ala  Gln  Asn  Gly  Ala  Glu  Asn
                    325                      330                     335

Val  Tyr  Gln  Thr  Asn  Ile  Glu  Gln  Asp  His  Ser  Arg  Ala  Glu  Asn  Thr
               340                      345                     350

Met  Ala  Ser  Glu  Leu  Leu  Arg  Ile  Leu  Ala  His  Leu  His  Ser  Met  Arg
               355                      360                     365

Val  Met  Asn  Gln  Ser  Ser  Val  Met  Ala  Ser  Asp  Pro  Thr  Ser  Ser  Leu
     370                      375                     380

Val  Ala  Met  Phe  Asp  Thr  Val  Ala  Thr  Ile  Thr  Val  Gln  Pro  Arg  Ile
385                      390                     395                          400

Pro  Phe  Thr  Ala  Thr  Val  Asp  Ser  Ala  Ile  Lys  Met  Val  Gln  Tyr  Arg
               405                      410                     415

Asp  Ser  Leu  Thr  Ala  Gly  Phe  Thr  Leu  Gln  Leu  Val  Thr  Gln  Met  Thr
               420                      425                     430
```

( 2 ) INFORMATION FOR SEQ ID NO:12:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:12:

```
Gly  Xaa  Gly  Xaa  Xaa  Gly
1                5
```

( 2 ) INFORMATION FOR SEQ ID NO:13:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

```
Glu  Xaa  Xaa  Tyr  Xaa  Xaa
1                5
```

( 2 ) INFORMATION FOR SEQ ID NO:14:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:14:

Asp  Xaa  Xaa  Tyr  Xaa  Xaa
   1                  5